US010098870B2

(12) United States Patent
Jia et al.

(10) Patent No.: US 10,098,870 B2
(45) Date of Patent: *Oct. 16, 2018

(54) POLYETHYLENE GLYCOL-CACTUS OLIGOPEPTIDE BONDING RAPAMYCIN DERIVATIVES

(71) Applicant: JENKEM TECHNOLOGY CO., LTD. (BEIJING), Haidan District, Beijing (CN)

(72) Inventors: Jianhuan Jia, Beijing (CN); Zewang Feng, Beijing (CN); Jinliang Wang, Beijing (CN); Yan Liu, Beijing (CN); Zhenguo Wang, Beijing (CN); Xuan Zhao, Beijing (CN)

(73) Assignee: JENKEM TECHNOLOGY CO., LTD. (BEIJING), Beijing (CN)

( * ) Notice: Subject to any disclaimer, the term of this patent is extended or adjusted under 35 U.S.C. 154(b) by 0 days.

This patent is subject to a terminal disclaimer.

(21) Appl. No.: 15/170,894

(22) Filed: Jun. 1, 2016

(65) Prior Publication Data

US 2016/0271116 A1    Sep. 22, 2016

Related U.S. Application Data

(63) Continuation of application No. PCT/CN2014/092646, filed on Dec. 1, 2014.

(30) Foreign Application Priority Data

Dec. 2, 2013 (CN) .......................... 2013 1 0632830

(51) Int. Cl.
| | |
|---|---|
| *A61K 31/436* | (2006.01) |
| *A61K 47/48* | (2006.01) |
| *A61P 35/00* | (2006.01) |
| *A61P 37/00* | (2006.01) |
| *C07D 498/18* | (2006.01) |
| *C08G 65/331* | (2006.01) |
| *C08G 65/333* | (2006.01) |

(52) U.S. Cl.
CPC ...... *A61K 31/436* (2013.01); *A61K 47/48215* (2013.01); *A61K 47/48338* (2013.01); *C07D 498/18* (2013.01); *C08G 65/331* (2013.01); *C08G 65/3311* (2013.01); *C08G 65/33303* (2013.01); *C08G 65/33396* (2013.01); *C08G 2650/30* (2013.01); *C08L 2203/02* (2013.01)

(58) Field of Classification Search
CPC .............. C07D 498/18; C08G 65/331; C08G 2650/30; C08G 65/3311; C08G 65/33303; C08G 65/33396; C08L 2203/02; A61K 31/436; A61K 47/48215; A61K 47/48338
See application file for complete search history.

(56) References Cited

U.S. PATENT DOCUMENTS

| | | | |
|---|---|---|---|
| 2005/0147617 A1* | 7/2005 | Ji | ..................... A61K 47/48338 |
| | | | 424/178.1 |
| 2007/0212371 A1* | 9/2007 | Gu | ..................... C07D 498/18 |
| | | | 424/193.1 |

FOREIGN PATENT DOCUMENTS

| | | | | |
|---|---|---|---|---|
| CN | 103083680 A | * | 5/2013 | ....... A61K 47/48215 |
| WO | WO 2005/092898 A1 | * | 10/2005 | ............. A61K 31/34 |

OTHER PUBLICATIONS

Machine translation of WO 2005/092898 A1, accessed Feb. 21, 2017, pp. 1-23.*
Machine translation of CN 103083680 A, accessed Feb. 14, 2017, pp. 1-25.*
Cloughesy et al, Antitumor Activity of Rapamycin in a Phase I Trial for Patients with Recurrent PTEN-Deficient Glioblastoma, PLoS Med, 2008, 5: e8, pp. 0139-0151.*
Turecek et al, PEGylation of Biopharmaceuticals: A Review of Chemistry and Nonclinical Safety Information of Approved Drugs, Journal of Pharmaceutical Sciences, 2016, 105, pp. 460-475.*
Veronese et al, PEGylation, successful approach to drug delivery, DDT, 2005, 10, pp. 1451-1458.*

* cited by examiner

*Primary Examiner* — Julie Ha
*Assistant Examiner* — Li N Komatsu
(74) *Attorney, Agent, or Firm* — Flener IP & Business Law; Zareea B. Flener

(57) ABSTRACT

The present invention provides compounds represented by formula (I) and pharmaceutical acceptable salts thereof, preparation method therefor and pharmaceutical composition containing the compounds represented by formula (I) and pharmaceutical acceptable salts thereof. In the compounds of the present invention, each terminal group of polyethylene glycol molecule can bond with a plurality of rapamycin molecules by cactus oligopeptide, with the loading rate of the pharmaceutical being increased. The compounds can be used to induce immunosuppression and treat graft rejection, autoimmune disease, solid tumors, fungal infection, and cardiovascular and cerebrovascular disease.

$$MI-A^2-(A^1)_m-X-PEG$$
$$|$$
$$A^2$$
$$|$$
$$MI$$

I

4 Claims, 4 Drawing Sheets

POLYETHYLENE GLYCOL-CACTUS OLIGOPEPTIDE BONDING RAPAMYCIN DERIVATIVES

CROSS-REFERENCE TO RELATED APPLICATION

The application is a continuation of PCT/CN2014/092646 (filed on Dec. 1, 2014), which claims priority from CN Patent Application Serial No. 201310632830.1 (filed on Dec. 2, 2013), the entire contents of which are incorporated herein by reference for all purposes.

FIELD OF THE INVENTION

The present invention relates to polyethylene glycol-cactus oligopeptide bonding rapamycin derivatives, preparation method thereof and pharmaceutical composition containing them. The present invention further relates to the use of these compounds to induce immunosuppression and treat graft rejection, graft versus host disease, autoimmune disease, inflammation, adult T-cell leukemia/lymphoma, solid tumors, fungal infection, cardiovascular disease, cerebrovascular disease, peripheral vascular disease or vascular hyperproliferative disease.

BACKGROUND OF THE INVENTION

Rapamycin (also known as "sirolimus") is a triene macrolide antibiotic produced by *Streptomyces hygroscopicus*, found in the soil on Easter Island, Chile in 1975. Rapamycin has an antifungal activity, particularly can against *Candida albicans*, both in vitro and in vivo. Rapamycin has a significant immunosuppressive activity which can be used for prophylaxis of allergic encephalomyelitis, multiple sclerosis and reactive arthritis. Rapamycin can also be used for prophylaxis and treatment of systemic lupus erythematosus, pneumonia, insulin-dependent diabetes mellitus, skin diseases (e.g. psoriasis), intestinal disorders, smooth muscle cell proliferation and vascular injury caused by intimal thickening, adult T-cell leukemia/lymphoma, ophthalmia, malignant cancer, inflammatory heart disease and anemia, etc. Rapamycin was developed by American Wyeth Company, and approved the listing for immunotherapy of patients after kidney transplantation by U.S. Food and Drug Administration (FDA) in 1999.

Rapamycin is the earliest mTOR (mammalian target of rapamycin) inhibitor ($IC_{50}$=1.7 μmol/L) discovered, with a half-life of 40~50 h in human body. In 1999 the FDA approved rapamycin as an immunosuppressive agent for kidney transplantation. In 2003 rapamycin was approved for drug-eluting stents by the FDA due to its anti coronary artery restenosis effect. In many tumor tissues and animal models, such as leukemia, breast cancer, pancreatic cancer, melanoma, small cell lung cancer, liver cancer, etc., rapamycin could concentration-dependently inhibit tumor cell growth.

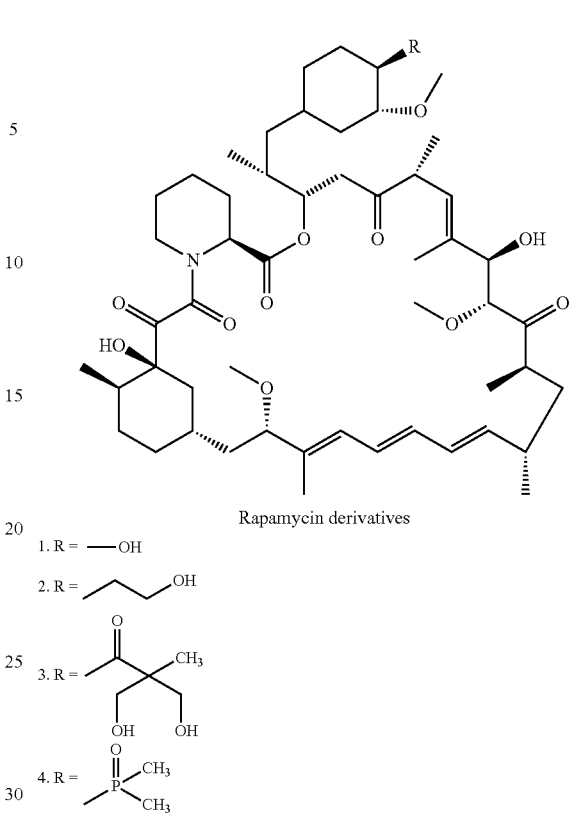

Rapamycin derivatives
1. R = —OH
2. R = ⁀⁀OH
3. R = (with CH₃, OH, OH)
4. R = (phosphonate with CH₃, CH₃)

Although rapamycin shows good prospects in clinical application, it still has a low bioavailability (<15%), poor water-solubility and other defects, a number of rapamycin derivatives with a high efficiency and specificity such as everolimus (2), temsirolimus (3), ridaforolimus (4) and the like were further developed in the late 1990s.

Everolimus (RAD001,2), that is 42-O-(2-hydroxyethyl)-rapamycin, is a novel oral mTOR inhibitor, with a better water-solubility than that of rapamycin, however, experiments have shown that everolimus had a poor oral bioavailability (about 15% to 30%), and half-life of 16~19 h in human body. Temsirolimus (CCI-779,3) is obtained after the hydroxyl group on the 42th position of rapamycin being esterifed with 2,2-bis(hydroxymethyl) propionic acid, temsirolimus is suitable for *intravenous* administration, and it is hydrolyzed to be rapamycin in vivo with a half-life of 13~15 h.

Ridaforolimus (deforolimus, AP23573, MK-8668, 4) is a semi-synthetic derivative designed by CADD with an inhibition activity against mTOR.

In addition to rapamycin derivatives have been listed and in clinical research stage, according to principle of prodrug, many studies of structure modification for rapamycin by small molecular groups are conducted, such as U.S. Pat. No. 6,342,507, US20050026868, US20050101624, U.S. Pat. No. 5,432,183, etc., a hydroxyl group, alkyl group, amino group or phosphoric acid group, etc., is introduced into rapamycin and its derivatives to achieve of purpose of increasing the water-solubility or enhancing the stability.

Polyethylene glycol (PEG) is a neutral polymer with a linear type or branched chains and various molecular weights and can be dissolved in water and majority of organic solvents. PEG is a viscous colorless liquid when its molecular weight is less than 1000; and it is a ceraceous white solid with a higher molecular weight, and the melting point of the solid is raised with increasing molecular weight and no longer increases until reaching 67° C. PEG is nontoxic in vivo and it is a pharmaceutical polymer material accepted by the FDA and collected in Chinese, British, American and other national pharmacopoeia. It is reported that PEGylation of organic molecules can increase the water-solubility thereof and impart other beneficial properties, such as improved half-life in plasma, improved biological distribution and reduced toxicity.

In U.S. Pat. Nos. 5,955,457, 5,780,462, 6,432,973, 6,331,547 and International Patent WO2007/103348, the preparation of conjugates of PEG with rapamycin and its derivatives is described. PEG or a mercapto derivative thereof is used to be linded with modified rapamycin or a derivative thereof to form a water-soluble derivative of rapamycin. Although this modification method could improve the water-solubility of rapamycin, a low loading rate for drug is obtained because each terminal group of polyethylene glycol molecule is bonded with only one drug molecule which causes great pressure on pharmaceutical preparations.

In Chinese Patent CN 02106691, CN 03801105, CN 200410048016 and CN200610150011, a method for preparation of a prodrug derivative by bonding polyethylene glycol with drug molecule through a cactus oligopeptide is described, wherein the drug mentioned include paclitaxel which is a terpenes compound and camptothecin which is an alkaloids compound, etc. Because of the two or more carboxyl groups in cactus oligopeptide which can bond with two or more drug molecules, therefore this method can greatly improve the loading rate of drug molecules on polyethylene glycol molecule. However, because of a large molecular structure of rapamycin and two reactive hydroxyl groups in the molecular structure, when the esterification reaction of rapamycin with polyethylene glycol-cactus oligopeptide is conducted, an incomplete reaction is easily obtained and a phenomenon of a rapamycin bonding with a plurality of polyethylene glycol molecules may appear, thus resulting in a reduced loading rate and complex reaction products, meanwhile the references described above do not disclose a group of —CO—CH$_2$— as the linking group between PEG molecule and oligopeptide.

In the present invention previous experiment methods are improved: (1) first conducting an esterification connection of a small molecule fragment containing a carboxyl group and a latent amino group with rapamycin, and the reaction product is a small molecule compound which can be purified by conventional chemical methods such as separation on columns; (2) then converting the latent amino group into an amino group to give an amino acid ester of rapamycin by reduction, hydrolysis and the like methods; (3) finally conducting an amidation connection of the amino acid ester of rapamycin with polyethylene glycol-cactus oligopeptide, since the nucleophilicity of an amino group is much stronger than that of an alcoholic hydroxyl group, so the amidation reaction can be carried out more easily and more completely than the esterification reaction, and remaining hydroxyl groups of rapamycin are substantially non-reactive due to a much weaker activity thereof than that of an amino group. The improved method can not only improve the loading rate on polyethylene glycol, but also obtain a rapamycin derivative with a comparatively single structure.

SUMMARY OF THE INVENTION

One aspect of the present invention is to provide a compound of formula I, or a pharmaceutically acceptable salt thereof:

wherein:

MI is a residue of an immunosuppressive macrolide, having a structure of formula II:

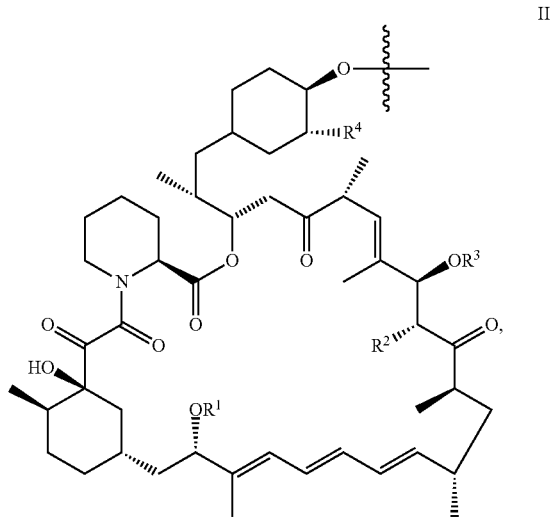

wherein, $R^1$ is selected from the group consisting of hydrogen, $C_1$-$C_{10}$ straight or branched alkyl, $C_2$-$C_{10}$ straight or branched alkenyl, $C_6$-$C_{12}$ substituted or unsubstituted aryl and $C_7$-$C_{12}$ substituted or unsubstituted aralkyl;

$R^2$ is selected from the group consisting of hydrogen, hydroxyl and $C_1$-$C_{10}$ straight or branched alkoxyl;

$R^3$ is selected from the group consisting of hydrogen, $C_1$-$C_{10}$ straight or branched alkyl, $C_2$-$C_{10}$ straight or branched alkenyl, $C_6$-$C_{12}$ substituted or unsubstituted aryl, $C_7$-$C_{12}$ substituted or unsubstituted aralkyl and —C(O)$R^{31}$, wherein $R^{31}$ is selected from the group consisting of hydrogen, $C_1$-$C_{10}$ straight or branched alkyl, $C_2$-$C_{10}$ straight or branched alkenyl, $C_6$-$C_{12}$ substituted or unsubstituted aryl, $C_7$-$C_{12}$ substituted or unsubstituted aralkyl;

$R^4$ is selected from the group consisting of hydrogen, hydroxyl and $C_1$-$C_{10}$ straight or branched alkoxyl;

$(A^1)_m$ represents a polycarboxylic oligopeptide, wherein $A^1$ represents residues of the same or different polycarboxy amino acids constituting the said polycarboxylic oligopeptide, the said polycarboxy amino acid contains two or more carboxyl groups and an amino group, and one of the carboxyl groups and the said amino group are attached to the same carbon atom; m is an integer of 2-12 representing the degree of polymerization of the said polycarboxylic oligopeptide;

$A^2$ has a structure of following formula, in the said structure the carboxyl is linked with MI and the amino is linked with the said polycarboxylic oligopeptide:

$$-\overset{H}{N}+\overset{R_5}{\underset{R_6}{C}}\!\!\underset{a}{\phantom{C}}\overset{O}{\overset{\|}{C}}-O-,$$

wherein, $R^5$ and $R^6$ are the same or different, selected from hydrogen, $C_1$-$C_6$ substituted or unsubstituted alkyl; a is an integer of 1-5;

PEG represents polyethylene glycol with a structure of straight-chain, Y-type or multi-branch, and a number average molecular weight of 300-60,000 Daltons;

X has a structure of following formula:

$$-\!\!+\!CH_2\!\!\xrightarrow{}_b\!\overset{O}{\overset{\|}{C}}\!-\!,$$

wherein, b is an integer of 0-6.

In some embodiments, the said $R_1$ is preferably selected from hydrogen, $C_1$-$C_6$ straight alkyl, more preferably selected from hydrogen, methyl, ethyl.

In some embodiments, the said $R_2$ is preferably selected from hydrogen, hydroxyl and $C_1$-$C_6$ straight alkoxyl, more preferably selected from —$OCH_3$, —$OCH_2CH_3$, —$O(CH_2)_2\,CH_3$.

In some embodiments, the said $R_3$ is preferably selected from hydrogen, $C_1$-$C_6$ straight alkyl, $C_2$-$C_{10}$ straight alkenyl, phenyl, halophenyl, benzyl, phenethyl, —$C(O)R^{31}$, wherein $R^{31}$ is selected from hydrogen, $C_1$-$C_6$ straight alkyl, $C_2$-$C_{10}$ straight alkenyl, phenyl, halophenyl, benzyl, phenethyl, more preferably selected from hydrogen, —$OCH_3$, —$OCH_2CH_3$, —$O(CH_2)_2CH_3$.

In some embodiments, the said $R_4$ is preferably selected from hydrogen, hydroxyl and $C_1$-$C_6$ straight alkoxyl, more preferably selected from —$OCH_3$, —$OCH_2CH_3$, —$O(CH_2)_2\,CH_3$.

In some embodiments, the said polycarboxylic oligopeptide has a structure of following formula:

$$\underset{H_2N}{\overset{HOOC}{\diagdown}}\!\!CH\!\!-\!\!\underset{R^8}{\overset{R^7}{\underset{|}{\overset{|}{C}}}}\!\!\xrightarrow{}_c\!COOH,$$

wherein, $R^7$ and $R^8$ are the same or different, selected from hydrogen, methyl, ethyl, n-propyl and isopropyl;

c is an integer of 1-10.

In some embodiments, both IC and $R^8$ are hydrogen.

In some embodiments, c is 2, the said compound has a structure of formula III:

$$MI\!-\!A^2\!\!+\!\!\overset{O}{\overset{\|}{C}}\!-\!\!\underset{\underset{\underset{\underset{MI}{|}}{\overset{|}{A^2}}}{\underset{|}{\overset{|}{C=O}}}}{\overset{H}{\underset{|}{C}}}\!\!-\!\!\overset{H}{\underset{|}{N}}\!\!\xrightarrow{}_m\!X\!-\!PEG.$$

III

In some embodiments, m is 2 or 3.
In some embodiments, a is 1.
In some embodiments, the said $A^2$ is a residue of amino acid selected from the group consisting of glycine, alanine, leucine, isoleucine, valine, proline, phenylalanine, methionine, serine, threonine, cysteine and tyrosine.

In some embodiments, the said $A^2$ is a residue of glycine, i.e., both $R_5$ and $R_6$ are hydrogen, a is 1.

In some embodiments, b is 1.
In some embodiments, the said PEG has a straight-chain structure of the following formula:

$$CH_3O\!\!-\!\!\!+\!CH_2CH_2O\!\!\xrightarrow{}_{\overline{n}},$$

wherein n is an integer greater than zero, and the said PEG has a number average molecular weight of 300-60,000 Daltons.

In some embodiments, PEG has a number average molecular weight of 10,000-20,000 Daltons, and a more preferable number average molecular weight of 20,000 Daltons.

In some embodiments, the said PEG has a Y-type structure of the following formula:

$$\begin{array}{c}CH_3O\!-\!\!+\!CH_2CH_2O\!\xrightarrow{}_{\overline{n}}\!-\!CH_2CH_2\\ \diagdown\\ \phantom{xxxxxxxxxxxxxxxxxxxxxxxx}N\!-\!,\\ \diagup\\ CH_3O\!-\!\!+\!CH_2CH_2O\!\xrightarrow{}_{\overline{n}}\!-\!CH_2\!-\!\overset{O}{\overset{\|}{C}}\end{array}$$

wherein n is an integer greater than zero, and the said PEG has a number average molecular weight of 300-60,000 Daltons.

In some embodiments, PEG has a number average molecular weight of 10,000-40,000 Daltons, and a more preferable number average molecular weight of 20,000-40,000 Daltons.

In some embodiments, the said PEG has a multi-branched structure of the following formula:

$$R\!\!-\!\!\!+\!\!O\!\!-\!\!\!+\!CH_2CH_2O\!\!\xrightarrow{}_{\overline{n}}\!\!]_z$$

wherein n is an integer greater than zero;
R is a core molecule and a residue of the following polyhydroxy compound molecule selected from the group consisting of pentaerythritol, oligomeric pentaerythritol, glycerol, poly-glycerol, sorbitol, 1,2,4-butanetriol, methyl glucoside and sucrose;

In some embodiments, the said R is selected from

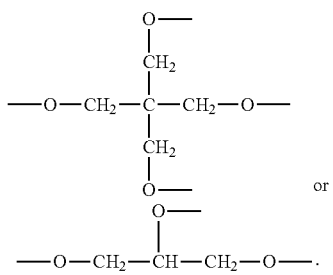

or z is an integer of 3-8 representing the number of branches;

The said PEG has a number average molecular weight of 300-60,000 Daltons.

In some embodiments, z is 4.

In some embodiments, the said polyethylene glycol has a number average molecular weight of 5,000-50,000 Daltons.

In some embodiments, the PEG has a number average molecular weight of 10,000-40,000 Daltons, and a more preferable number average molecular weight of 20,000-40,000 Daltons.

In some embodiments, $R^1$ is methyl, $R^2$ is methoxyl, $R^3$ is H, $R^4$ is methoxyl, the said compound is 42 esterified rapamycin derivative.

In some embodiments, the compound of the present invention is:

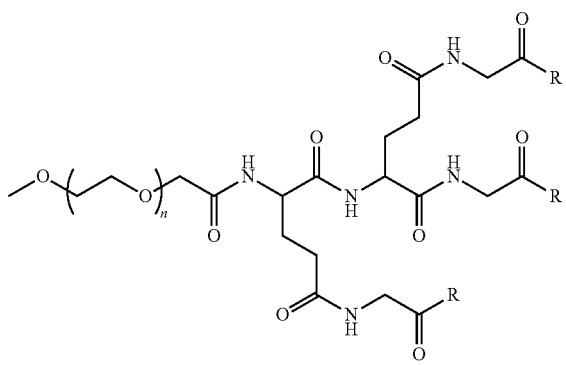

R =

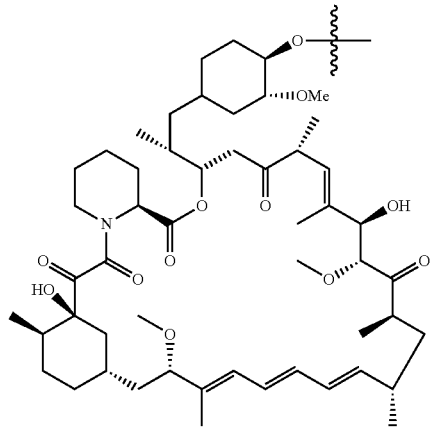

wherein n is an integer of 200-1,000, preferably an integer of 200-500.

In some embodiments, the compound of the present invention is:

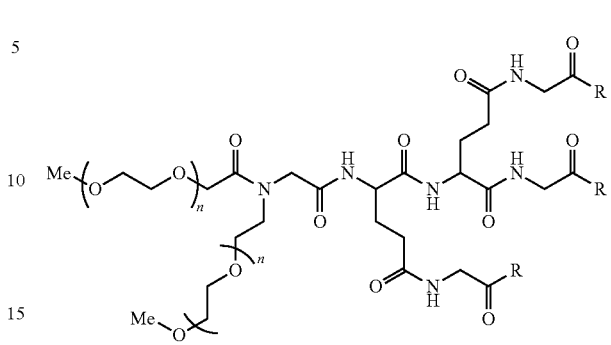

R =

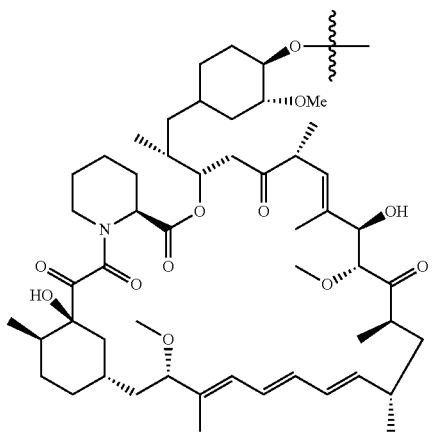

wherein n is an integer of 100-500, preferably an integer of 100-250.

Another aspect of the present invention is to provide a method for preparing the compound of formula I, wherein, the said method comprising the steps as follow:

(1) conducting an esterification reaction of a compound IV

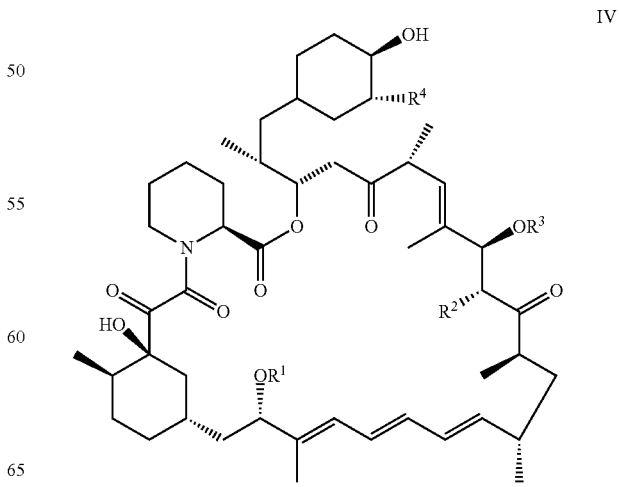

with a compound V

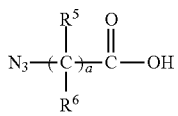

to obtain a compound VI

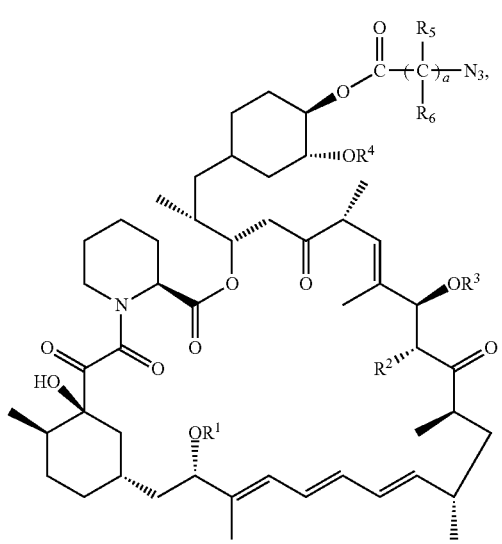

(2) conducting a reduction reaction of said compound VI to obtain a compound VII

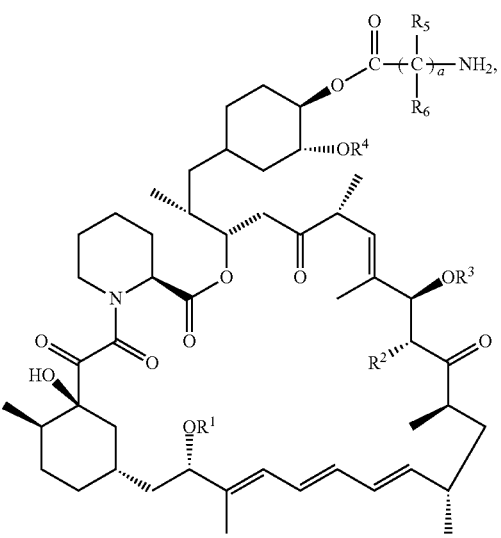

(3) conducting an amidation reaction of said compound VII with a polyethylene glycol-oligopeptide VIII

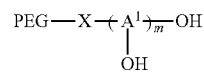

to obtain the compound of formula I.

In some embodiments, the said compound V is obtained by a reaction of

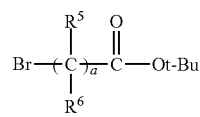

with $NaN_3$.

In some embodiments, in the said step (1) and (3), the said esterification reaction and said amidation reaction are conducted in the presence of a condensation agent, the said condensation agent is selected from the group consisting of N-hydroxy-7-azabenzotriazole, 1-hydroxybenzotriazol, 2-(7-azabenzotriazole)-N,N,N',N'-tetramethyluronium hexafluorophosphate, benzotriazole-N,N,N',N'-tetramethyluronium hexafluorophosphate), bis(2-oxo-3-oxazolidiny) phosphonic chloride, 1H-benzotriazol-1-yloxy-tris (1-pyrrolidinyl) phosphine hexafluorophosphate, 1,3-dicyclohexyl carbodiimide, N,N'-carbonyldiimidazole, 1-ethyl-(3-dim ethyl aminopropyl) carbodiimide, N,N'-diisopropyl carbodiimide, 4-dimethylaminopyridine and combinations thereof.

In some embodiments, in the said step (2), the said reduction reaction is conducted in the presence of a reducing agent, the said reducing agent is selected from the group consisting of triphenylphosphine, hydrogen, sodium borohydride, zinc borohydride, lithium aluminum hydride, dichloro-dimethyl-sulfhydryl-borane, alkaline earth metals, metallic indium, metallic samarium, metallic tin, metallic zinc, hydrazine, metallic iron, ferrous salts, aluminum triiodide and tetrathiomolybdates.

Another aspect of the present invention is to provide use of a compound as described in the present invention or a pharmaceutically acceptable salt thereof in treatment or inhibition of graft rejection or graft versus host disease, solid tumor, fungal infection, rheumatoid arthritis, multiple sclerosis, cardiac valve restenosis or pneumonia in a mammal.

Another aspect of the present invention is to provide a pharmaceutical composition comprising a compound as described in the present invention or a pharmaceutically acceptable salt thereof and a pharmaceutically acceptable carrier or excipient.

In some embodiments, the dosage form of the said pharmaceutical composition is tablet, capsule, pill, granule, powder, suppository, injection, solution, suspension, ointment, patch, lotion, drop, liniment or aerosol.

Anti-tumor activity of the compounds of the present invention could be verified by standard pharmacological test procedures using compound LPR-2 and LPR-3, as representative compounds of the present invention, which could measure the inhibition level of growth of human hepatoma cells (plc/prf/5). The results obtained from the standard pharmacological test procedures showed that the compounds of the present invention could inhibit growth of tumor and could be used as antineoplastic drugs. Specifically, the compounds of the present invention can be used for treating or inhibiting the growth of solid tumors, including sarcomas and carcinomas, such as astrocytoma, liver cancer, prostate cancer, breast cancer, lung cancer and ovarian cancer.

The compound of the present invention may also be used for treating or inhibiting graft rejection, such as the transplantation of kidney, heart, liver, lung, bone marrow, pancreas, cornea, small intestine, etc., skin allograft, cardiac valve xenograft, etc.; may also be used for treating or inhibiting graft versus host disease; and may also be used for treating or inhibiting autoimmune diseases such as lupus, rheumatoid arthritis, diabetes, severe muscle weakness and multiple sclerosis; and inflammation such as psoriasis, dermatitis, eczema, enteritis and pneumonia, etc.; adult T-cell leukemia/lymphoma; fungal infections; hyperproliferative vascular disease, cardiac valve restenosis, transplanted vascular atherosclerosis; and cardiovascular disease, cerebrovascular disease, peripheral vascular disease, coronary artery disease; and used for inhibiting stroke or multiple infarct dementia.

When used for cardiac valve restenosis, it is preferred to be used for treating cardiac valve restenosis occurs after the operation of angioplasty, and the compounds of the present invention may be administrated before, during or after the operation.

When the compound is used to treat or inhibit a particular disease state or disorder, it should be understood that the effective amount of the compounds described in the present invention may be dependent on and change with the specific compound used, administration mode, symptom and its severity, as well as a variety of factors related to the individual being treated.

In an embodiment of the present invention, use of a compound as described in the present invention or a pharmaceutically acceptable salt thereof in prophylaxis, treatment and/or inhibiting of graft rejection or graft versus host disease, solid tumor, fungal infection, rheumatoid arthritis, multiple sclerosis, cardiac valve restenosis or pneumonia in a mammal is provided. Wherein, the said solid tumor is one of astrocytoma, liver cancer, prostate cancer, breast cancer, lung cancer or ovarian cancer. Preferably, the lung cancer is human small cell lung cancer.

In U.S. Pat. Nos. 5,955,457, 5,780,462, 6,432,973, 6,331,547 and International Patent WO 2007,103,348, each terminal group of polyethylene glycol could bond with only one molecule of rapamycin. In the present invention, polyethylene glycol is used to bond with cactus oligopeptide, followed by drug moleculars of rapamycin, enabling each terminal group of polyethylene glycol to bond with a plurality of rapamycin molecules, which could greatly increase drug loading rate on polyethylene glycol. A greatly reduced preparation specification may be obtained with the same dosage of administration; and a greatly increased amount of administration may be obtained with the same preparation specification. Therefore, the implementation of the present invention may increase not only the diversity of preparation species, but also the diversity of preparation specifications. In studies of screening for pharmacological activity, the inventors of the present invention have further discovered that polyethylene glycol-cactus oligopeptide bonding rapamycin (LPR-2 and LPR-3) had a stronger antitumor activity than that of polyethylene glycol-rapamycin (LPR-1). Polyethylene glycol used in LPR-2 and LPR-1 had both the same structure and the same number average molecular weight, while a cactus oligopeptide was added into the structure of LPR-2, and LPR-2 had a significantly better anticancer activity against subcutaneous transplantation tumor model of human hepatocellular carcinoma plc/prf/5 than that of LPR-1 with administrating by the same drug dose counting by rapamycin.

DETAILED DESCRIPTION OF THE INVENTION

Figure 1:
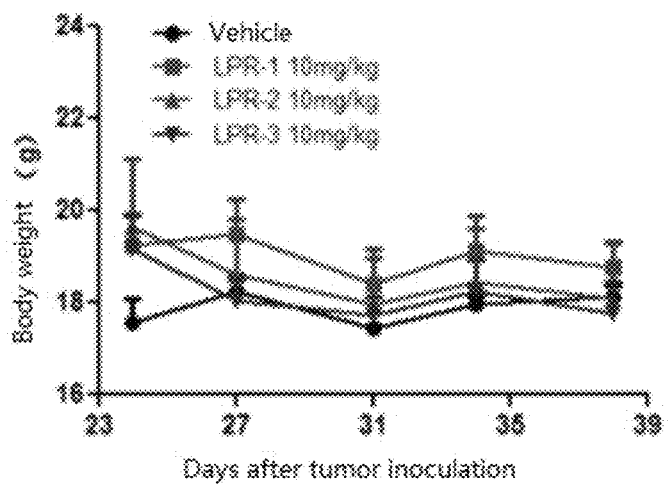
FIG. 1 shows the results of change in body weight of mice bearing human hepatoma cell plc/prf/5 caused by LPR-1, LPR-2, LPR-3 and vehicle.

Rapamycin shows good prospects in clinical application, but it still has a low bioavailability (<15%), poor water-solubility and other defects, a number of rapamycin derivatives with a high efficiency and specificity such as everolimus, temsirolimus, ridaforolimus and the like were further developed in the late 1990s, which are obtained by introducing polar groups into molecule of rapamycin to achieve the goal of enhancing the water-solubility of rapamycin. Rapamycin is so sensitive to acids and bases that it will be degraded even under physiological conditions, and the products obtained after degradation have no immunosuppressive activity, and it is a problem to be solved that how to increase the stability.

Rapamycin, due to the hydroxyl groups in its structure, can be esterified with polyethylene glycol-cactus oligopeptide to form a prodrug to obtain an improved water-solubility, accelerated distribution of drug molecules, as well as a better permeability to tumor to avoid an allergic reaction induced by local aggregation of the drug; additionally, the polyethylene glycol fragment can form a hydrophilic barrier to prevent an excessive degradation of rapamycin, thus to obtain a rational use of rapamycin. Furthermore, a molecular conformation which is similar to but better than liposome is formed by chemically bonding of the drug with the amphiphilic substance to obtain an increase bioavailability of drug, reduced dosage, reduced side effects and prolonged duration of action by using the targeting towards tumors. Particularly, the pharmaceutically active ingredient is released by biodegradation of the ester group in vivo. The drug improved by this method has a good water-solubility, rapid onset, long duration and effective therapeutic effect.

Unlike the PEGylated rapamycin derivative in patent WO2007/103348, a cactus oligopeptide is used to enable rapamycin to bond with polyethylene glycol. The oligopeptide used in the present invention refers to a polypeptide comprising 2-12 amino acids, which can be completely hydrolyzed to be free amino acids by peptidase and enter the bloodstream in the form of free amino acids. Amino acids have a good biocompatibility, and is dispersible in vivo and safe after biodegradation, at the same time, the cactus oligopeptide can provide more reactive sites, a larger loading rate to bond with more drug moleculars and to increase the range of choice of polyethylene glycol used.

The conjugates according to the present invention may be administered in the form of pure compound or suitable pharmaceutical compositions with any acceptable modes of administration or regents for similar application. Thus, the conjugates according to the present invention may be administered orally, nasally, parenterally, topically, transdermally or rectally, in the form of solid, semi-solid, lyophilized powder, or liquid medicaments, e.g., tablets, capsules, pills, granules, powders, suppositories, injections, solutions, suspensions, ointments, patches, lotions, drops, liniments, aerosols, etc. The unit dosage forms which are suitable for precise and simple administration are preferred. The composition may contain conventional pharmaceutical carriers or excipients and conjugates according to the present invention as active ingredients (one or more), as well as other medicaments, carriers and adjuvants etc.

Generally, according to the desired mode of administration, the pharmaceutically acceptable composition contains the conjugate according to the present invention with a weight percentage of about 1 to about 99 and a suitable pharmaceutical excipient with a weight percentage of about 99 to 1. The composition comprising conjugate according to the present invention with a weight percentage of about 5 to 75 with the rest being a suitable pharmaceutical excipient is preferred.

The pharmaceutical compositions may be administered in liquid form, e.g. by dissolving or dispersing the conjugates according to the present invention (from about 0.5 to about 20%) and pharmaceutically acceptable adjuvants which are employed selectively into carriers to thereby form a solution or suspension, the examples of carrier are water, saline, glucose hydrate, glycerol and ethanol etc.

If necessary, the pharmaceutical compositions according to the present invention may also contain minor amounts of auxiliary substances such as wetting agents or emulsifiers, pH buffers, antioxidants, etc., for example: citric acid, sorbitan monolaurate, triethanolamine oleate and butylated hydroxy toluene, etc.

The following examples are used to illustrate the present invention but are not used to limit the present invention.

EXAMPLE

Rapamycin and L-(+)-glutamic acid used in the embodiments are purchased from Wuhan Yuanchenggongchuang Technology Co., Ltd. and Beijing Chemical Reagent Company, respectively, tert-butyl bromoacetate, triphenylphosphine, p-toluenesulfonic acid, benzyl alcohol and dicyclohexylcarbodiimide (DCC) are purchased from Sinopharm Chemical Reagent Co., Ltd., 4-dimethylaminopyridine (DMAP) and 1-hydroxy benzotriazole (HOBt) are purchased from Shanghai MEDPEP Co., Ltd., N-t-butoxycarbonyl-L-glutamic acid-5-benzyl ester is purchased from Sichuan Tongsheng Amino Acid Co., Ltd., monomethoxy polyethylene glycol acetic acid, monomethoxy polyethylene glycol-glutamic acid dipeptide, Y-type polyethylene glycol acetic acid are provided by Beijing Jenkem Technology Co., Ltd., other reagents are commercially available.

Example 1 Preparation of Glycine Ester of Rapamycin

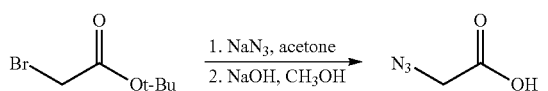

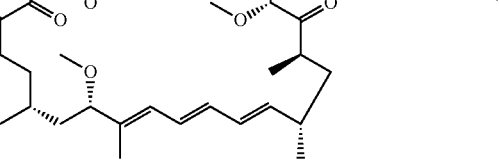

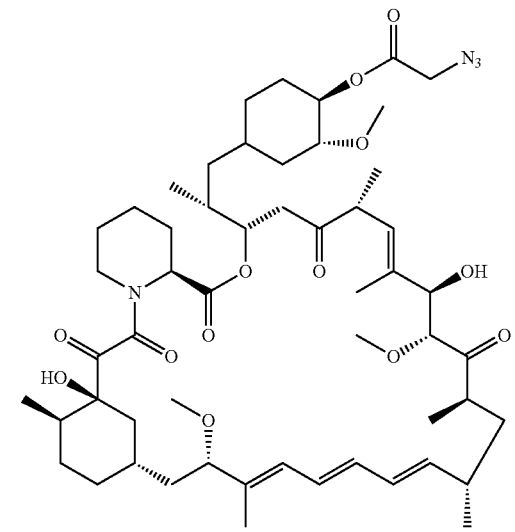

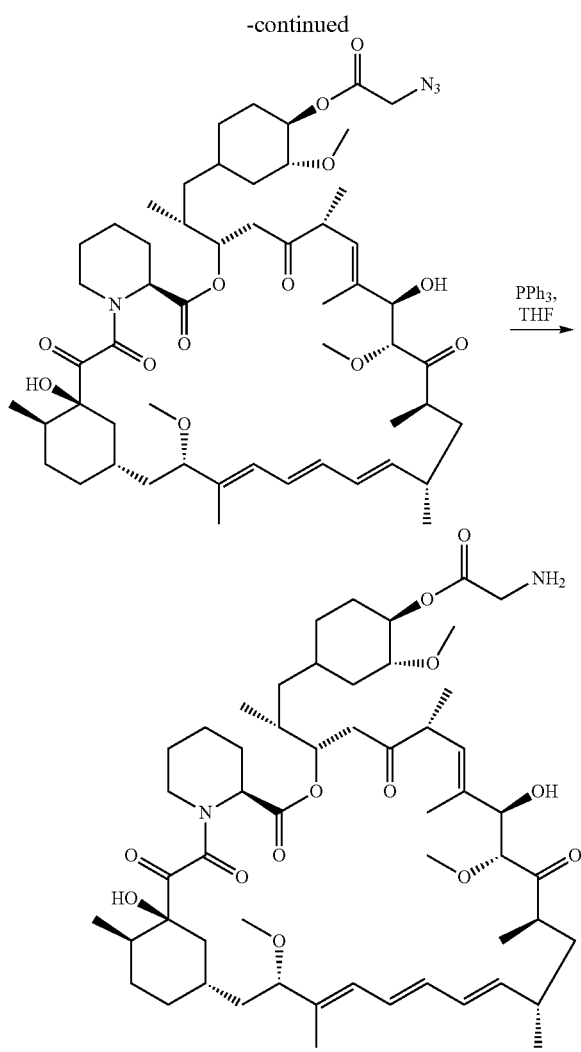

Tert-butyl bromoacetate (5.82 g, 30 mmoL) was added to the reaction flask and dissolved by acetone (80 mL), a solution obtained by sodium azide (4.55 g, 70 mmoL) dissolved in water (40 mL) was then added, the mixture obtained was heated and refluxed overnight. Acetone was distilled off the reaction solution, the residue was extracted with ether, the extract obtained was washed by saturated brine, dried and concentrated under reduced pressure to give an oily liquid. This liquid was dissolved by methanol (90 mL) and added by 1 N of sodium hydroxide solution (90 mL), stirred, heated and refluxed for 3 h. After being cooled, methanol was distilled off under reduced pressure, the residue was cooled by an ice bath and added by 6 N of hydrochloric acid to adjust the value of pH to 2, and then extracted with ether, the extract obtained was washed by water, dried, and concentrated to give azidoacetic acid, MS m/z: 124 [M+Na]$^+$.

Azidoacetic acid (253 mg, 2.5 mmoL) and rapamycin (2.28 g, 2.5 mmoL) were added to the reaction flask, dissolved with dichloromethane, cooled by an ice bath, and then 4-dimethylaminopyridine (DMAP, 611 mg, 5 mmoL) and N,N-dicyclohexylcarbodiimide (DCC, 1.03 g, 5 mmoL) were added to the reaction flask, the mixture was continued to be stirred at room temperature overnight after the addition. The residue obtained after concentration of the reaction solution was purified by column chromatography to give 1.42 g of azide acetate of rapamycin with a yield of 57%, MS m/z: 1020 [M+Na]+.

Azide acetate of rapamycin (0.7 g, 0.7 mmoL) and triphenylphosphine (0.37 g, 1.4 mmoL) were added to the reaction flask, then a mixture of tetrahydrofuran and water (5:1, 180 mL) was added, the reaction was heated to 50° C. overnight, the residue obtained after the concentration of reaction solution was extracted with ethyl acetate, the extract obtained was washed by saturated brine, dried. The residue obtained after concentration under reduced pressure was purified by column chromatography to give 0.48 g of glycine ester of rapamycin with a yield of 70%, MS m/z: 994 [M+Na]+.

Example 2 Preparation of Monomethoxy Polyethylene Glycol (with a Number Average Molecular Weight of 20,000)-Rapamycin Conjugate (LPR-1)

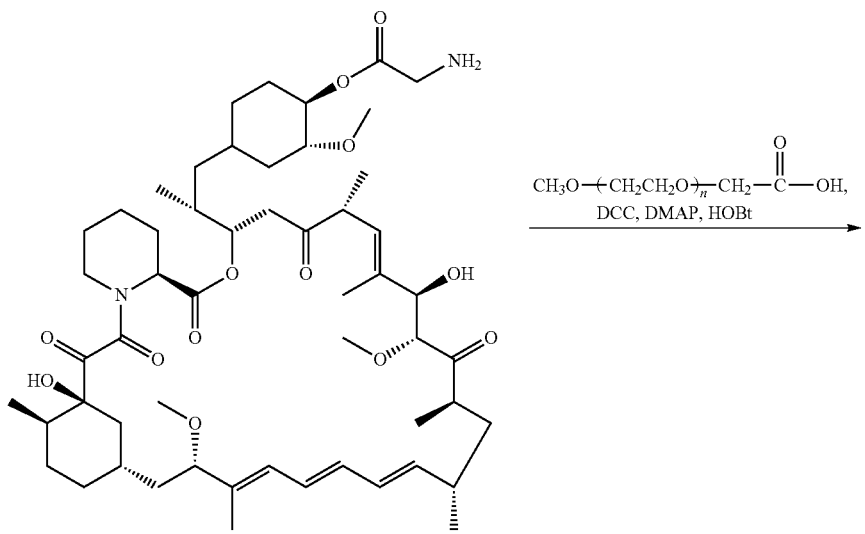

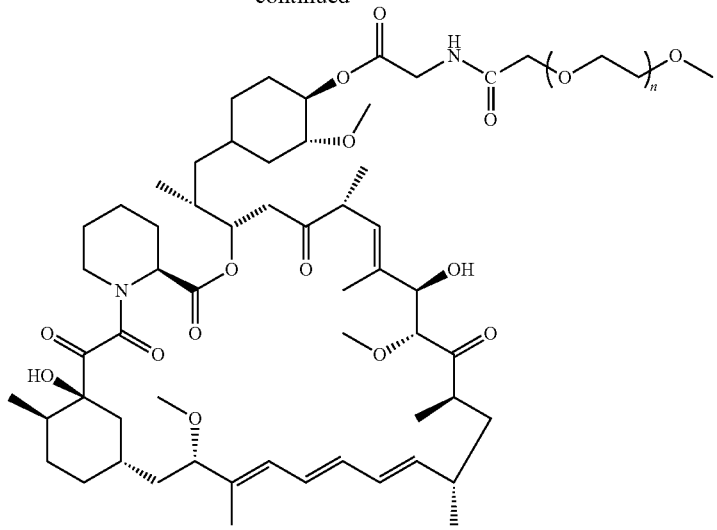

LPR-1

Monomethoxy polyethylene glycol acetic acid (20 K, 1 g, 0.05 mmoL), glycine ester of rapamycin (97 mg, 0.1 mmoL) prepared in Example 1, 1-hydroxy benzotriazole (HOBt, 6.8 mg, 0.05 mmoL) and DMAP (12.2 mg, 0.1 mmoL) were added to the reaction flask, dissolved with dichloromethane, cooled by an ice bath, then added dropwise by a solution obtained by DCC (15.5 mg, 0.075 mmoL) dissolved in dichloromethane, warmed to room temperature naturally after the dropping, the reaction was kept overnight, the next day the reaction solution was concentrated and the residue was crystallized with isopropanol to give 0.82 g of monomethoxy polyethylene glycol (20 K)-rapamycin conjugate (LPR-1) (n is about 450).

$^1$H-NMR (300 MHz, CDCl$_3$): 0.90 (Me, 3H, 43), 0.92 (Me, 3H, 49), 0.94 (Me, 3H, 46), 0.96 (Me, 3H, 48), 0.97 (Me, 3H, 45), 1.10 (CH$_2$, 2H, 24), 1.11 (CH$_2$, 2H, 36), 1.20 (CH$_2$, 2H, 42), 1.33 (CH$_2$, 2H, 41), 1.37 (CH, 1H, 37), 1.45 (CH$_2$, 2H, 5), 1.47 (CH$_2$, 2H, 4), 1.60 (CH$_2$, 2H, 13), 1.61 (CH$_2$, 2H, 12), 1.65 (CH$_2$, 2H, 15), 1.65 (CH$_2$, 2H, 44), 1.74 (Me, 3H, 47), 1.75 (CH, 1H, 35), 2.07 (CH, 4H, 3, 11, 23, 25), 2.08 (CH$_2$, 2H, 33), 3.14 (Me, 3H, 50), 3.33 (CH, 1H, 31), 3.36 (Me, 3H, 51), 3.37 (CH$_2$, 2H, 6), 3.42 (CH, 1H, 40), 3.44 (Me, 3H, 52), 3.56 (CH, 1H, 39), 3.64 (CH$_2$, 1800H, PEG), 3.71 (CH, 1H, 16), 3.72 (CH, 1H, 27), 3.86 (CH, 1H, 14), 4.17 (CH$_2$, 2H, 54), 4.19 (CH, 1H, 28), 5.16 (CH, 1H, 2), 5.17 (CH, 1H, 34), 5.29 (=CH, 1H, 30), 5.39 (=CH, 1H, 22), 5.95 (=CH, 1H, 18), 6.13 (=CH, 1H, 21), 6.31 (=CH, 1H, 20), 6.38 (=CH, 1H, 19), 8.34 (CH, 1H, 55).

Example 3 Preparation of Monomethoxy Polyethylene Glycol (with a Number Average Molecular Weight of 20,000)-Glutamic Acid Dipeptide-Rapamycin Conjugate (LPR-2)

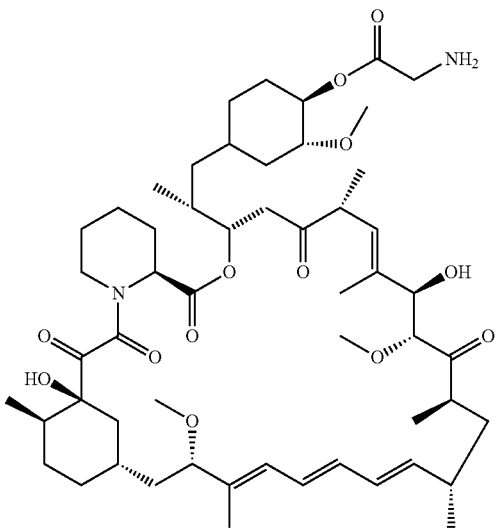

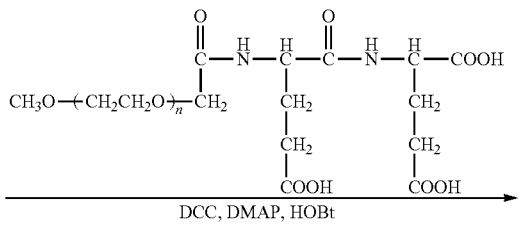

-continued

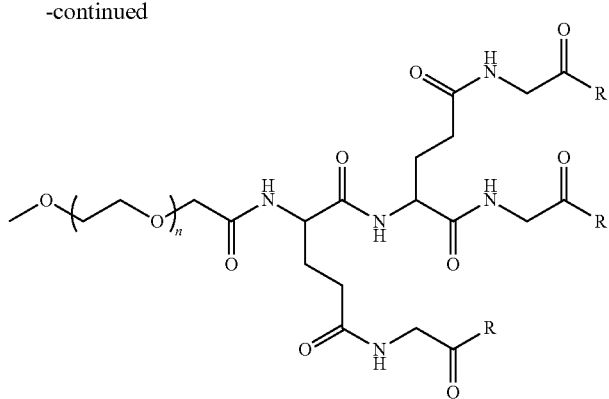

LPR-2

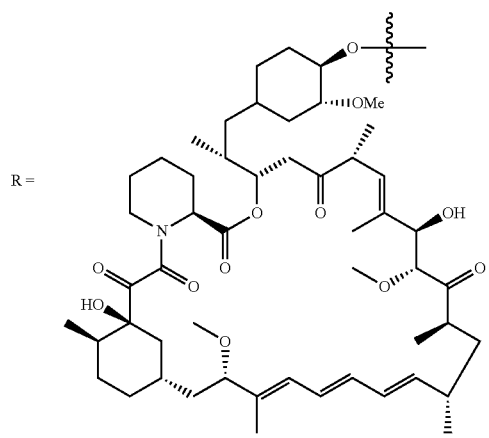

Monomethoxy polyethylene glycol-glutamic acid dipeptide (20 K, 0.5 g, 0.025 mmol), glycine ester of rapamycin 48.6 mg (0.05 mmoL) prepared in Example 1, HOBt (3.4 mg, 0.025 mmoL) and DMAP 6.1 mg (0.05 mmoL) were added to the reaction flask, dissolved with dichloromethane, cooled by an ice bath, then added dropwise by a solution obtained by DCC 15.5 mg (0.075 mmoL) dissolved in dichloromethane, warmed to room temperature naturally after the dropping, the reaction was kept overnight. The next day the reaction solution was concentrated and the residue was crystallized with isopropanol to give 0.41 g of monomethoxy polyethylene glycol (20K)-glutamic acid dipeptide-rapamycin conjugate (LPR-2) (n is about 450).

$^1$H-NMR (300 MHz, CDCl$_3$): 0.90 (Me, 9H, 43), 0.92 (Me, 9H, 49), 0.94 (Me, 9H, 46), 0.96 (Me, 9H, 48), 0.97 (Me, 9H, 45), 1.10 (CH$_2$, 6H, 24), 1.11 (CH$_2$, 6H, 36), 1.20 (CH$_2$, 6H, 42), 1.33 (CH$_2$, 6H, 41), 1.37 (CH, 3H, 37), 1.45 (CH$_2$, 6H, 5), 1.47 (CH$_2$, 6H, 4), 1.60 (CH$_2$, 6H, 13), 1.61 (CH$_2$, 6H, 12), 1.65 (CH$_2$, 6H, 15), 1.65 (CH$_2$, 6H, 44), 1.74 (Me, 9H, 47), 1.75 (CH, 3H, 35), 2.07 (CH, 12H, 3, 11, 23, 25), 2.08 (CH$_2$, 6H, 33), 3.14 (Me, 9H, 50), 3.33 (CH, 3H, 31), 3.36 (Me, 9H, 51), 3.37 (CH$_2$, 6H, 6), 3.42 (CH, 3H, 40), 3.44 (Me, 9H, 52), 3.56 (CH, 3H, 39), 3.64 (CH$_2$, 1800H, PEG), 3.71 (CH, 3H, 16), 3.72 (CH, 3H, 27), 3.86 (CH, 3H, 14), 4.17 (CH$_2$, 6H, 54), 4.19 (CH, 3H, 28), 5.16 (CH, 3H, 2), 5.17 (CH, 3H, 34), 5.29 (=CH, 3H, 30), 5.39 (=CH, 3H, 22), 5.95 (=CH, 3H, 18), 6.13 (=CH, 3H, 21), 6.31 (=CH, 3H, 20), 6.38 (=CH, 3H, 19), 8.34 (CH, 3H, 55).

Example 4 Preparation of Y-Type Polyethylene Glycol (with a Number Average Molecular Weight of 40,000)-Glutamic Acid Dipeptide-Rapamycin Conjugate (LPR-3)

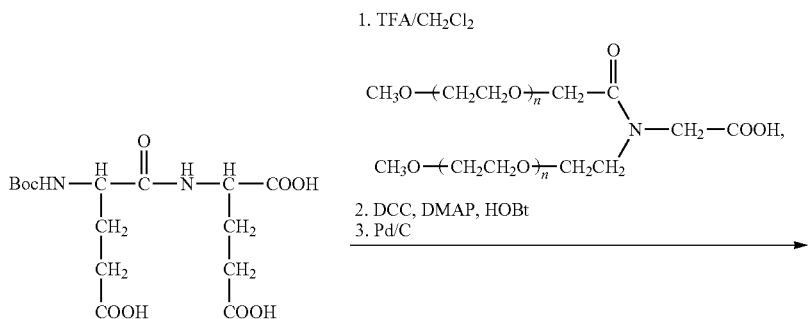

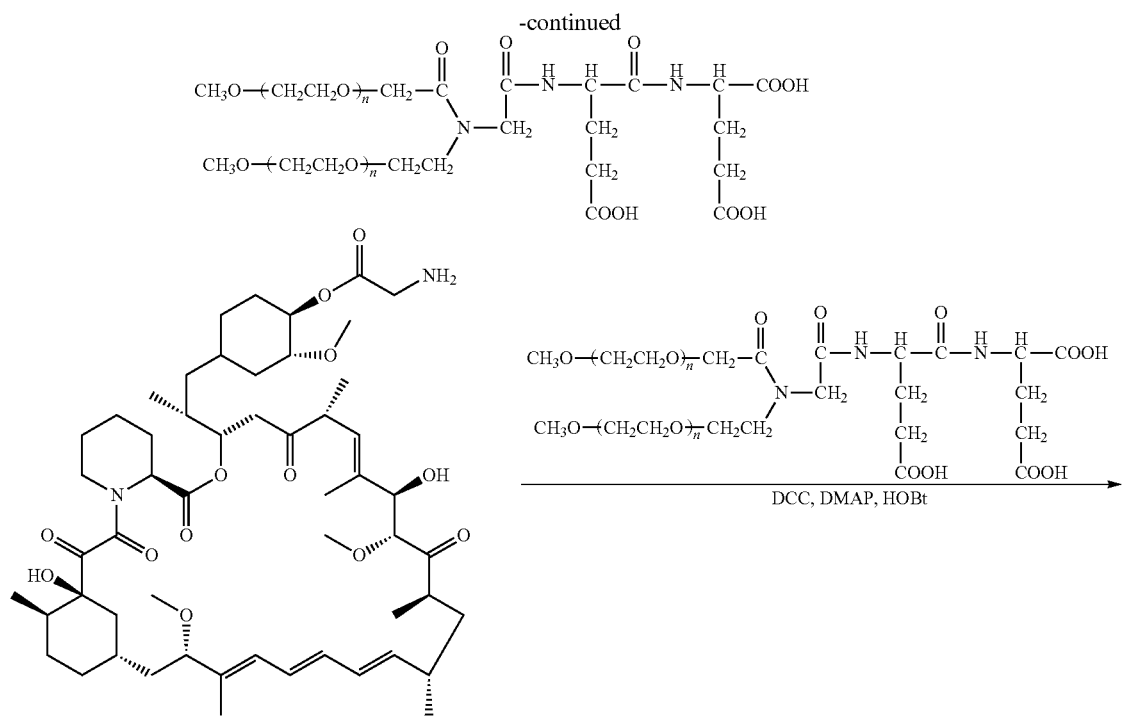
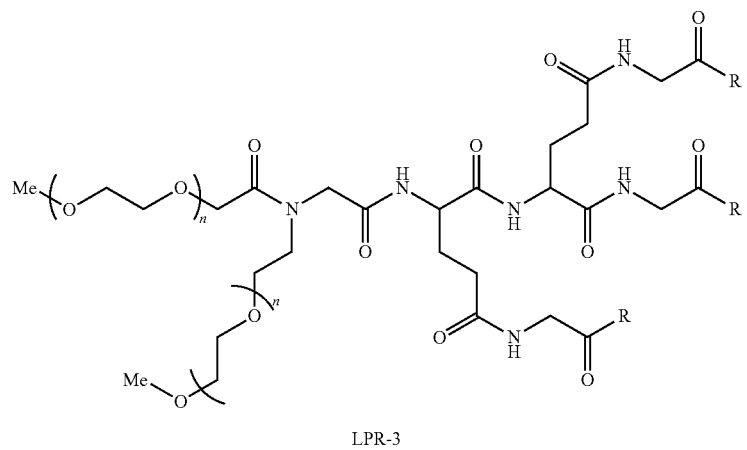
LPR-3
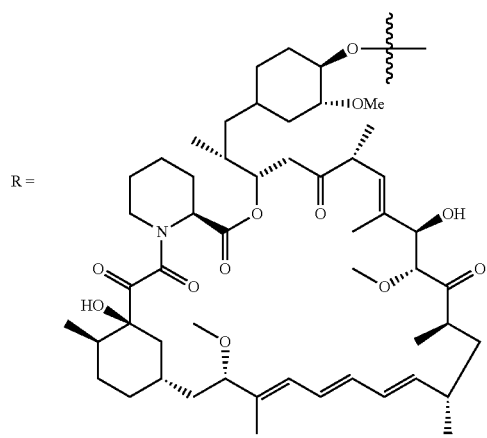
R =

N-t-butoxycarbonyl-benzyl glutamate dipeptide (0.78 g, 1.2 mmoL) (Example 3) was dissolved in dichloromethane (10 mL), added by 3 mL of trifluoroacetic acid, the reaction was kept at room temperature for 2 h. 100 mL of dichloromethane was added after removal of solvent, and sodium bicarbonate solution with a concentration of 5% was added to adjust the value of pH to 7-8. The reaction mixture was extracted and separated, the organic phase was washed with sodium bicarbonate solution with a concentration of 5% twice, dried with anhydrous sodium sulfate. The filtrate obtained after filtration was added directly to the reaction flask, and Y-type polyethylene glycol acetic acid (40 K, 40.0 g, 1 mmol), DMAP (245 mg, 2 mmol), HOBt (135 mg, 1 mmol) were added under the protection of nitrogen. After reactants being completely dissolved, DCC (412 mg, 2 mmol) was added. The reaction was stirred at room temperature overnight. The reaction mixture was filtered and rotary evaporated to remove the solvent, the residue obtained was added by 500 mL of isopropanol, filtered, and the product obtained was dried under vacuum. This product was dissolved in 200 mL of anhydrous methanol, added by 1.0 g of palladium on carbon and introduced by hydrogen overnight at room temperature. Palladium on carbon was removed by filtration, the solvent was removed by rotary evaporation, the residue obtained was added into 500 mL of isopropanol, filtered and dried under vacuum. 33.4 g of Y-type polyethylene glycol-glutamic acid dipeptide (40 K) was obtained.

Y-type polyethylene glycol-glutamic acid dipeptide (40 K, 0.5 g, 0.0125 mmol), glycine ester of rapamycin 24.3 mg (0.025 mmol) prepared in Example 1, HOBt (1.7 mg, 0.0125 mmo) and DMAP 3 mg (0.025 mmol) were added to the reaction flask, dissolved with dichloromethane, cooled by an ice bath, then added dropwise by a solution obtained by DCC 4.1 mg (0.02 mmol) dissolved in dichloromethane, the mixture was warmed to room temperature naturally after the dropping, the reaction was kept overnight. The next day the reaction solution was concentrated and the residue was crystallized with isopropanol to give 0.44 g of Y-type polyethylene glycol (40K)-glutamic acid dipeptide-rapamycin conjugate (LPR-3) (n is about 450).

1H-NMR (300 MHz, CDCl3): 0.90 (Me, 9H, 43), 0.92 (Me, 9H, 49), 0.94 (Me, 9H, 46), 0.96 (Me, 9H, 48), 0.97 (Me, 9H, 45), 1.10 (CH2, 6H, 24), 1.11 (CH2, 6H, 36), 1.20 (CH2, 6H, 42), 1.33 (CH2, 6H, 41), 1.37 (CH, 3H, 37), 1.45 (CH2, 6H, 5), 1.47 (CH2, 6H, 4), 1.60 (CH2, 6H, 13), 1.61 (CH2, 6H, 12), 1.65 (CH2, 6H, 15), 1.65 (CH2, 6H, 44), 1.74 (Me, 9H, 47), 1.75 (CH, 3H, 35), 2.07 (CH, 12H, 3, 11, 23, 25), 2.08 (CH2, 6H, 33), 3.14 (Me, 9H, 50), 3.33 (CH, 3H, 31), 3.36 (Me, 9H, 51), 3.37 (CH2, 6H, 6), 3.42 (CH, 3H, 40), 3.44 (Me, 9H, 52), 3.56 (CH, 3H, 39), 3.64 (CH2, 1800H, PEG), 3.71 (CH, 3H, 16), 3.72 (CH, 3H, 27), 3.86 (CH, 3H, 14), 4.17 (CH2, 6H, 54), 4.19 (CH, 3H, 28), 5.16 (CH, 3H, 2), 5.17 (CH, 3H, 34), 5.29 (=CH, 3H, 30), 5.39 (=CH, 3H, 22), 5.95 (=CH, 3H, 18), 6.13 (=CH, 3H, 21), 6.31 (CH, 3H, 20), 6.38 (=CH, 3H, 19), 8.34 (CH, 3H, 55).

Example 5 the Inhibitory Activity of Different Polyethylene Glycol-Cactus Oligopeptide-Rapamycin Conjugates Against Tumor Cells (1) Experimental Method and Procedure (a) Cell Culture Plc/prf/5 cells were cultured with a monolayer in vitro in MEM medium supplied with heat-inactivated fetal bovine serum with a volume ratio of 10%, and an incubator at 37° C. with the air containing $CO_2$ with a proportion of 5%. The tumor cells were passaged with digestion by trypsin-EDTA twice a week. The cells in the exponential growth phase were collected, counted, and used for inoculation.

(b) Inoculation of Tumor Cells, Grouping and Administration $1 \times 10^7$ of plc/prf/5 tumor cells were suspended in 0.1 ml of mixed solution (PBS:Matrigel=4:1), inoculated to each NOD/SCID mouse at the right shoulder. 24 days later the mean tumor volume was desired to reach about 350 mm³, the mice with a smaller or larger tumor were removed and the remaining mice were divided into groups randomly according to tumor size and administrated.

(c) Experimental Scheme

TABLE 1

The grouping and dosage regimen of experimental animals

| Group | N | Compound used for treatment | Dosage [a] (mg/kg) | Dosing volume (µl/g) | Route of administration | Dosage regimen |
|---|---|---|---|---|---|---|
| 1 | 5 | Vehicle control | — | 10 | i.v. | Q2W × 2W |
| 2 | 5 | LPR-1 | 10 mg/kg | 10 | i.v. | Q2W × 2W |
| 3 | 5 | LPR-2 | 10 mg/kg | 10 | i.v. | Q2W × 2W |
| 4 | 5 | LPR-3 | 10 mg/kg | 10 | i.v. | Q2W × 2W |

[a] The dosage is counted with rapamycin, the same below.

Wherein Q2W×2W represents intravenous injection twice a week for 2 weeks, the same below.

(2) Experimental Results (a) Body Weight

Changes in body weight of tumor-bearing mice in each treatment group are shown in Table 2 and FIG. 1.

TABLE 2

The body weight of each treatment group at different time points

| | Body weight of animal (g)[a] | | | |
|---|---|---|---|---|
| Days after inoculation | Vehicle control | LPR-1 10 mg/kg | LPR-2 10 mg/kg | LPR-3 10 mg/kg |
| 24 | 17.6 ± 0.5 | 19.2 ± 0.7 | 19.6 ± 1.5 | 19.2 ± 0.7 |
| 27 | 18.3 ± 0.3 | 19.5 ± 0.8 | 18.6 ± 1.2 | 18.0 ± 0.4 |
| 31 | 17.4 ± 0.1 | 18.4 ± 0.6 | 18.0 ± 1.2 | 17.7 ± 0.4 |
| 34 | 18.0 ± 0.2 | 19.1 ± 0.8 | 18.5 ± 1.2 | 18.2 ± 0.7 |
| 38 | 18.1 ± 0.2 | 18.8 ± 0.5 | 18.1 ± 1.2 | 17.8 ± 0.7 |

Note:
[a] mean value ± standard error (b) Tumor Volume

Figure 2:
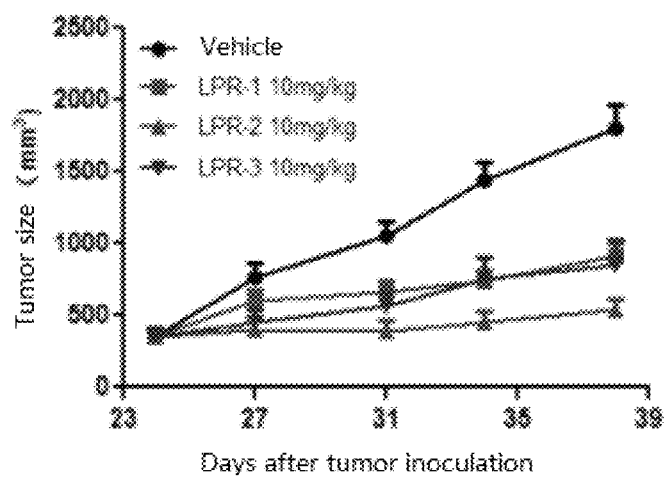
FIG. 2 shows the results of antitumor activity of LPR-1, LPR-2, LPR-3 and vehicle against subcutaneous transplantation tumor model of human hepatoma cell plc/prf/5.

Changes in tumor volume of each treatment group are shown in Table 3 and FIG. 2.

TABLE 3

The tumor volume of each treatment group at different time points

| Days after inoculation | Tumor volume (mm³)[a] | | | |
|---|---|---|---|---|
| | Vehicle control | LPR-1 10 mg/kg | LPR-2 10 mg/kg | LPR-3 10 mg/kg |
| 24 | 355 ± 64 | 352 ± 49 | 353 ± 54 | 358 ± 62 |
| 27 | 763 ± 102 | 598 ± 80 | 404 ± 89 | 455 ± 85 |
| 31 | 1048 ± 104 | 670 ± 74 | 391 ± 72 | 569 ± 100 |
| 34 | 1439 ± 130 | 738 ± 74 | 456 ± 77 | 754 ± 151 |
| 38 | 1801 ± 162 | 919 ± 78 | 536 ± 77 | 848 ± 178 |

Note:
[a]mean value ± standard error (c) Evaluation of Anti-Tumor Effect

The evaluation indexes of anti-tumor effect of LPR 1,2,3 on subcutaneous transplantation tumor model of plc/prf/5 are shown in Table 4.

TABLE 4

Evaluation of anti-tumor effect of each treatment group

| Group | Tumor volume (mm³)[a] | Tumor control rate T/C (%) | Days for delaying tumor growth (to 1000 mm³) | P value |
|---|---|---|---|---|
| Vehicle control | 1801 ± 162 | — | — | — |
| LPR-1 (10 mg/kg) | 919 ± 78 | 51 | 7 | 0.000 |
| LPR-2 (10 mg/kg) | 536 ± 77 | 30 | >7 | 0.000 |
| LPR-3 (10 mg/kg) | 848 ± 178 | 47 | >7 | 0.000 |

Note:
[a]mean value ± standard error (3) Summary and Discussion of Experimental Results In the experiment, the pesticide effects in vivo of LPR-1, LPR-2 and LPR-3 on subcutaneous transplantation tumor model of human hepatoma cell plc/prf/5 were evaluated. The tumor volume of each treatment group at different time points is shown in Table 2 and FIG. 2. 38 days later after inoculation of plc/prf/5 tumor cells to NOD/SCID mice, the tumor volume of the vehicle control group reached 1801 mm³. The test compounds LPR-1, LPR-2 and LPR-3 showed a certain anti-tumor effect, wherein LPR-2 showed obviously the maximum anti-tumor effect with a T/C value less than 40%, and p value of 0.000 representing a significant difference compared with the vehicle control group.

Effect of changes in body weight of tumor-bearing mice in each treatment group is shown in Table 1 and FIG. 1. No obvious toxic reaction of each treatment group was observed during the experiment.

In summary, in this study, the test drugs LPR-1, LPR-2 and LPR-3 showed an anti-tumor effect on subcutaneous transplantation tumor model of human hepatoma cell plc/prf/5, wherein LPR-2 showed obviously the maximum anti-tumor effect, no obvious toxic reaction of each treatment group was observed during the experiment. The polyethylene glycol used in LPR-1 and LPR-2 had the same structure and number average molecular weight, but in structure of LPR-1 polyethylene glycol bonded with rapamycin only through glycine molecular causing that each terminal group of polyethylene glycol bonding with only one rapamycin molecular; while in structure of LPR-2 polyethylene glycol bonded with rapamycin through glutamic acid dipeptide and glycine causing that each terminal group of polyethylene glycol bonding with three rapamycin molecular. LPR-2 had a drug loading rate 3 times as much as that of LPR-1, and anti-tumor effect significantly higher than that of LPR-1.

Example 6 the Inhibitory Activity of Monomethoxy Polyethylene Glycol (with a Number Average Molecular Weight of 20,000)-Glutamic Acid Dipeptide-Rapamycin Conjugate (LPR-2) and Reference Substance Against PLC/PRF/5 Hepatoma Cells (1) Experimental Method and Procedure (a) Cell Culture Plc/prf/5 cells were cultured with a monolayer in vitro in MEM medium supplied with heat-inactivated fetal bovine serum with a volume ratio of 10%, and an incubator at 37° C. with the air containing $CO_2$ with a proportion of 5%. The tumor cells were passaged with digestion by trypsin-EDTA twice a week. The cells in the exponential growth phase were collected, counted, and used for inoculation.

(b) Inoculation of Tumor Cells, Grouping and Administration $8.32 \times 10^6$ of plc/prf/5 tumor cells were suspended in 0.1 ml of mixed solution (PBS:Matrigel=6:4), inoculated to each nude mouse at the right shoulder, and there were totally 36 mice inoculated. 10 days later the mean tumor volume was desired to reach about 161 mm³, the mice with a smaller or larger tumor were removed and the remaining 24 mice were divided into groups randomly according to tumor volume and administrated.

(c) Experimental Scheme

TABLE 5

The grouping and dosage regimen of experimental animals

| Group | N | Compound used for treatment | Dosage (mg/kg) | Dosing volume (μl/g) | Route of administration | Dosage regimen |
|---|---|---|---|---|---|---|
| 1 | 6 | Physiological saline | — | 10 | i.v. | QW × 4W |
| 2 | 6 | 5-FU | 25 | 10 | i.v. | QD × 5 |
| 3 | 6 | LPR-2 | 30 | 10 | i.v. | BIW × 4W |
| 4 | 6 | LPR-2 | 45 | 15 | i.v. | QW × 4W |

Wherein QW×4W represents intravenous injection once a week for 4 weeks, BIW×4W represents intravenous injection once every two weeks for 4 weeks, the same below.

(2) Experimental Results (a) Body Weight

LPR-2 and 5-FU had an effect on body weight of mice bearing xenograft tumor model of plc/prf/5.

Figure 3:
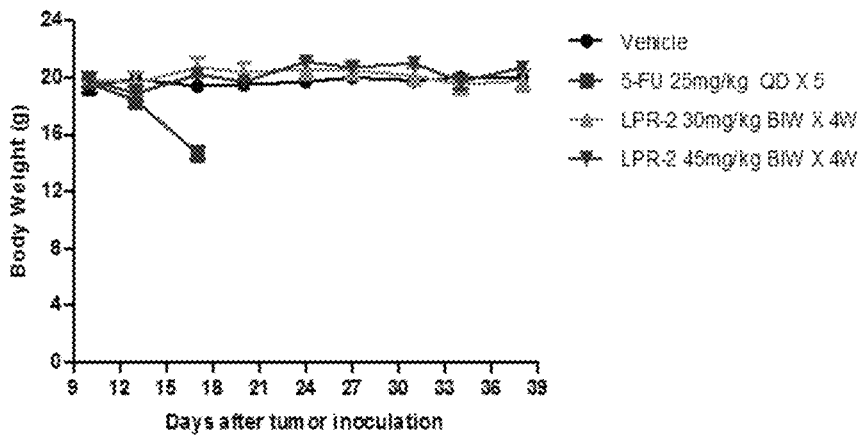
FIG. 3 shows the results of change in body weight of mice bearing human hepatoma cell PLC/PRF/5 caused by LPR-2 and reference substance.

Changes in body weight of tumor-bearing mice in each treatment group are shown in Table 6 and FIG. 3.

TABLE 6

The body weight of each treatment group at different time points

| Days after inoculation | Body weight of animal (g)[a] | | | |
|---|---|---|---|---|
| | Physiological saline | 5-FU 25 mg/kg | LPR-2 30 mg/kg | LPR-2 45 mg/kg |
| 10 | 19.4 ± 0.5 | 19.6 ± 0.3 | 19.9 ± 0.5 | 19.8 ± 0.5 |
| 13 | 19.9 ± 0.4 | 18.4 ± 0.5 | 19.6 ± 0.8 | 18.9 ± 0.5 |
| 17 | 19.4 ± 0.2 | 14.7 ± 0.5 | 20.7 ± 0.7 | 20.2 ± 0.3 |
| 20 | 19.5 ± 0.2 | | 20.4 ± 0.6 | 19.7 ± 0.3 |
| 24 | 19.7 ± 0.4 | | 20.6 ± 0.7 | 21.1 ± 0.3 |
| 27 | 20.0 ± 0.2 | | 20.5 ± 0.6 | 20.7 ± 0.2 |
| 31 | 19.8 ± 0.2 | | 20.1 ± 0.6 | 21.0 ± 0.2 |
| 34[b] | 20.0 ± 0.3 | | 19.5 ± 0.6 | 19.7 ± 0.5 |
| 38 | 20.0 ± 0.4 | | 19.8 ± 0.7 | 20.7 ± 0.3 |

Note:
[a]mean value ± standard error;
[b]last administration.

(b) Tumor Growth

Figure 4:
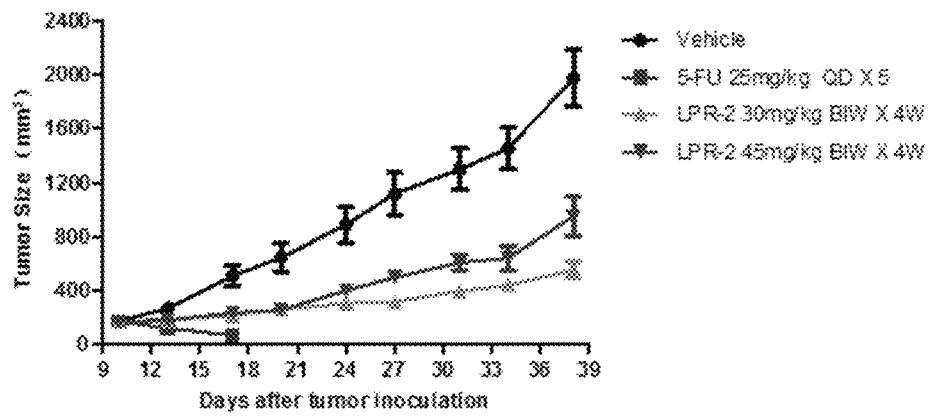
FIG. 4 shows the results of antitumor activity of LPR-2 and reference substance against subcutaneous transplantation tumor model of human hepatoma cell PLC/PRF/5.

Changes in tumor volume of each treatment group are shown in Table 7 and FIG. 4.

TABLE 7

The tumor volume of each treatment group at different time points

| Days after inoculation | Tumor volume (mm³)[a] | | | |
|---|---|---|---|---|
| | Physiological saline | 5-FU 25 mg/kg | LPR-2 30 mg/kg | LPR-2 45 mg/kg |
| 10 | 171 ± 18 | 170 ± 16 | 171 ± 15 | 171 ± 19 |
| 13 | 269 ± 37 | 118 ± 7 | 176 ± 11 | 180 ± 25 |
| 17 | 507 ± 77 | 69 ± 4 | 217 ± 25 | 234 ± 28 |
| 20 | 645 ± 105 | | 260 ± 30 | 257 ± 24 |
| 24 | 886 ± 130 | | 303 ± 32 | 399 ± 25 |
| 27 | 1,119 ± 156 | | 317 ± 42 | 496 ± 39 |
| 31 | 1,299 ± 154 | | 395 ± 39 | 607 ± 60 |
| 34[b] | 1,455 ± 157 | | 437 ± 44 | 640 ± 93 |
| 38 | 1,973 ± 211 | | 553 ± 63 | 948 ± 144 |

Note:
[a]mean value ± standard error;
[b]last administration.

(c) Evaluation of Anti-Tumor Effect

The evaluation indexes of anti-tumor effect of LPR-2 and 5-FU on xenograft tumor model of plc/prf/5 are shown in Table 8.

TABLE 8

Evaluation of anti-tumor effect of each treatment group

| Group | N[a] | Tumor volume (mm³)[b] | | RTV[b] | Tumor weight (mg)[b] | TGD (to 1,000 mm³) | T/C (%) | | P value | |
|---|---|---|---|---|---|---|---|---|---|---|
| | | 10th day | 38th day | (38th day) | (38th day) | | RTV | TW[c] | RTV | TW[c] |
| Physiological saline | 6 | 171 ± 18 | 1,973 ± 211 | 12.05 ± 1.63 | 1877 ± 195 | 0 | 100 | 100 | 1.000 | 1.000 |
| LPR-2 (30 mg/kg) | 6 | 171 ± 15 | 553 ± 63 | 3.48 ± 0.68 | 517 ± 67 | >12 | 29 | 27 | 0.000 | 0.000 |
| LPR-2 (45 mg/kg) | 6 | 171 ± 19 | 948 ± 144 | 5.61 ± 0.67 | 845 ± 87 | >12 | 46 | 45 | 0.001 | 0.000 |

Note:
[a]the number of surviving animals in each group after completion of the treatment;
[b]Mean ± SEM;
[c]TW (Tumor Weight).

(3) Summary and Discussion of Experimental Results

In the experiment, the pesticide effect in vivo of LPR-2 on subcutaneous transplantation tumor model of human hepatoma cell plc/prf/5 in immune deficiency mice was evaluated. The tumor volume of each treatment group at different time points is shown in Table 7 and FIG. 4. 38 days later after inoculation of plc/prf/5 tumor cells, the tumor volume and tumor weight of the physiological saline control group reached 1973 mm³ and 1877 mg, respectively.

The 5-FU positive control group (25 mg/kg) showed an obvious anti-tumor effect, but was so toxic with this dosage that all the animals died. Two groups of LPR-2 with different dosages (30 and 45 mg/kg) had significant anti-tumor effect, with tumor volume of 553 and 948 mm³, respectively, at the end of experiment, and T/C values of 29% and 46% and p values of 0.000 and 0.001, compared with the physiological saline group. The analysis result of tumor weight was consistent with the tumor volume.

Effect of changes in body weight of tumor-bearing mice in each group is shown in Table 6 and FIG. 3. No abnormality in each group administrated with LPR-2 before or after administration was observed and body weight remained stable during the administration period.

In summary, in this study, the test drug LPR-2 with dosages of 30 and 45 mg/kg showed significant anti-tumor effect on xenograft tumor model of human hepatoma cell plc/prf/5, and the animals treated with LPR-2 showed a good tolerance and no death of animals occurred in the treatment group. The positive drug 5-FU had a significant toxicity and the whole group of animals died.

Example 7 the Inhibitory Activity of Monomethoxy Polyethylene Glycol (with a Number Average Molecular Weight of 20,000)-Glutamic Acid Dipeptide-Rapamycin Conjugate (LPR-2) and Reference Substance Against Hep3B Hepatoma Cells (1) Experimental Method and Procedure (a) Cell Culture Hep3B cells were cultured with a monolayer in vitro in MEM medium supplied with heat-inactivated fetal bovine serum with a volume ratio of 10%, and an incubator at 37° C. with the air containing $CO_2$ with a proportion of 5%. The tumor cells were passaged with digestion by trypsin-EDTA twice a week. The cells in the exponential growth phase were collected, counted, and used for inoculation.

(b) Inoculation of Tumor Cells, Grouping and Administration $5.67 \times 10^6$ of Hep3B tumor cells were suspended in 0.1 ml of mixed solution (PBS:Matrigel=7:3), inoculated to each mouse at the right shoulder, and there were totally 37 mice inoculated. 16 days later the mean tumor volume was desired to reach about 453 mm³, the mice with a smaller or larger tumor were removed and the remaining 24 mice were divided into groups randomly according to tumor volume and administrated.

(c) Experimental Scheme

TABLE 9

The grouping and dosage regimen of experimental animals

| Group | N | Compound used for treatment | Dosage (mg/kg) | Dosing volume (μl/g) | Route of administration | Dosage regimen |
|---|---|---|---|---|---|---|
| 1 | 6 | Physiological saline | — | 10 | i.v. | QW × 4W |
| 2 | 6 | 5-FU | 15 | 10 | i.v. | (QD × 5) × 2W |
| 3 | 6 | LPR-2 | 30 | 10 | i.v. | BIW × 4W |
| 4 | 6 | LPR-2 | 45 | 15 | i.v. | QW × 4W |

(2) Experimental Results (a) Body Weight

LPR-2 and 5-FU had an effect on body weight of mice bearing xenograft tumor model of Hep3B.

Figure 5:
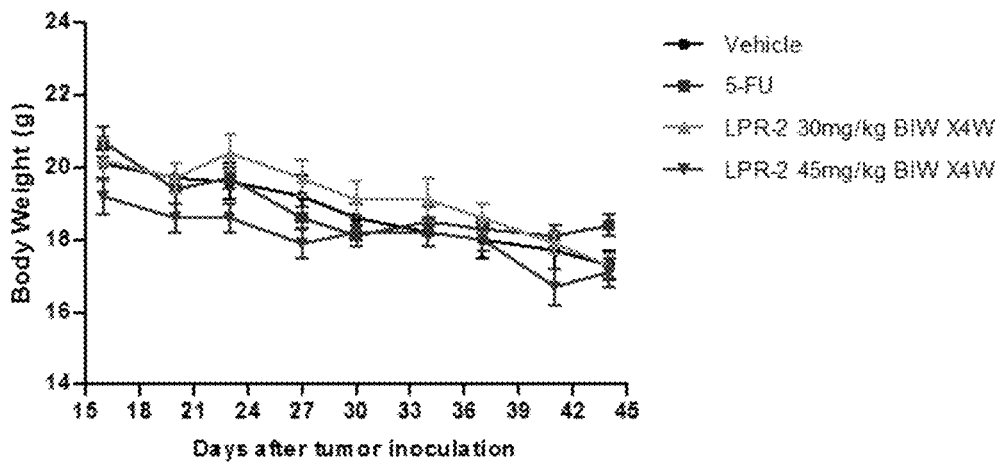
FIG. 5 shows the results of change in body weight of mice bearing human hepatoma cell Hep3B caused by LPR-2 and reference substance.

Changes in body weight of tumor-bearing mice in each treatment group are shown in Table 10 and FIG. 5.

TABLE 10

The weight of each treatment group at different time points

| Days after inoculation | Body weight of animal (g)[a] | | | |
|---|---|---|---|---|
| | Physiological saline | 5-FU 15 mg/kg | LPR-2 30 mg/kg BIW × 4W | LPR-2 45 mg/kg QW × 4W |
| 16 | 20.1 ± 0.4 | 20.7 ± 0.4 | 20.2 ± 0.6 | 19.2 ± 0.5 |
| 20 | 19.7 ± 0.4 | 19.4 ± 0.4 | 19.7 ± 0.4 | 18.6 ± 0.4 |
| 23 | 19.6 ± 0.5 | 19.7 ± 0.3 | 20.4 ± 0.5 | 18.6 ± 0.4 |
| 27 | 19.2 ± 0.6 | 18.6 ± 0.3 | 19.7 ± 0.5 | 17.9 ± 0.4 |
| 30 | 18.6 ± 0.4 | 18.1 ± 0.3 | 19.1 ± 0.5 | 18.2 ± 0.4 |
| 34 | 18.2 ± 0.4 | 18.5 ± 0.4 | 19.1 ± 0.6 | 18.2 ± 0.4 |
| 37 | 18.0 ± 0.5 | 18.3 ± 0.3 | 18.6 ± 0.4 | 18.0 ± 0.3 |
| 41[b] | 17.7 ± 0.5 | 18.1 ± 0.3 | 17.9 ± 0.3 | 16.7 ± 0.5 |
| 44 | 17.3 ± 0.4 | 18.4 ± 0.3 | 17.3 ± 0.3 | 17.1 ± 0.4 |

Note:
[a] mean value ± standard error;
[b] last administration.

(b) Tumor Growth

Figure 6:
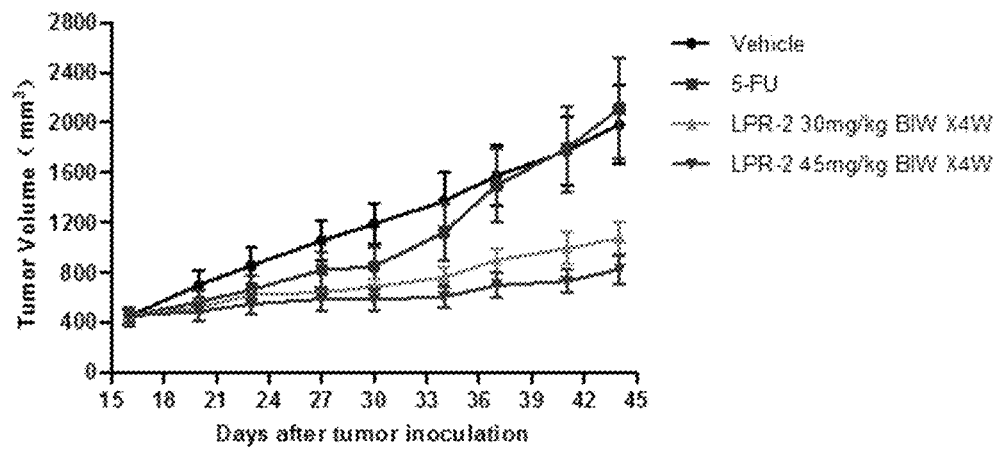
FIG. 6 shows the results of antitumor activity of LPR-2 and reference substance against subcutaneous transplantation tumor model of human hepatoma cell Hep3B.

Changes in tumor volume of each treatment group are shown in Table 11 and FIG. 6.

TABLE 11

The tumor volume of each treatment group at different time points

| Days after inoculation | Tumor volume (mm³)[a] | | | |
|---|---|---|---|---|
| | Physiological saline | 5-FU 15 mg/kg | LPR-2 30 mg/kg BIW × 4W | LPR-2 45 mg/kg QW × 4W |
| 16 | 453 ± 72 | 453 ± 66 | 454 ± 60 | 453 ± 56 |
| 20 | 701 ± 116 | 567 ± 84 | 524 ± 47 | 490 ± 73 |
| 23 | 860 ± 147 | 667 ± 105 | 622 ± 37 | 549 ± 83 |
| 27 | 1,056 ± 157 | 820 ± 149 | 643 ± 45 | 589 ± 91 |
| 30 | 1,192 ± 163 | 850 ± 150 | 689 ± 57 | 584 ± 87 |
| 34 | 1,374 ± 225 | 1,123 ± 226 | 761 ± 82 | 608 ± 89 |
| 37 | 1,576 ± 239 | 1,500 ± 295 | 899 ± 97 | 699 ± 102 |
| 41[b] | 1,775 ± 274 | 1,793 ± 342 | 995 ± 126 | 733 ± 93 |
| 44 | 1,984 ± 317 | 2,114 ± 395 | 1,074 ± 130 | 827 ± 112 |

Note:
[a] mean value ± standard error;
[b] last administration.

(c) Evaluation of Anti-Tumor Effect

The evaluation indexes of anti-tumor effect of LPR-2 and 5-FU on xenograft tumor model of Hep3B are shown in Table 12.

TABLE 12

Evaluation of anti-tumor effect of each treatment group

| Group | $N^a$ | Tumor volume $(mm^3)^b$ 16th day | Tumor volume $(mm^3)^b$ 44th day | $RTV^b$ (44th day) | Tumor weight $(mg)^b$ (44th day) | TGD (to 1,000 $mm^3$) | T/C (%) RTV | T/C (%) $TW^c$ | P value RTV | P value $TW^c$ |
|---|---|---|---|---|---|---|---|---|---|---|
| Physiological saline | 6 | 453 ± 72 | 1,984 ± 317 | 5.00 ± 0.95 | 1555 ± 267 | 0 | 100 | 100 | 1.000 | 1.000 |
| 5-Fu (15 mg/kg) | 6 | 453 ± 66 | 2,114 ± 395 | 4.53 ± 0.32 | 1695 ± 289 | 6 | 106 | 109 | 0.996 | 0.999 |
| LPR-2 (30 mg/kg) BIW × 4W | 6 | 454 ± 60 | 1,074 ± 130 | 2.43 ± 0.19 | 720 ± 94 | 17 | 54 | 46 | 0.177 | 0.113 |
| LPR-2 (45 mg/kg) QW × 4W | 6 | 453 ± 56 | 827 ± 112 | 1.85 ± 0.17 | 625 ± 84 | >17 | 42 | 40 | 0.089 | 0.075 |

Note:
$^a$the number of surviving animals in each group after completion of the treatment;
$^b$Mean ± SEM;
$^c$TW (Tumor Weight).

(3) Summary and Discussion of Experimental Results

In the experiment, the pesticide effect in vivo of LPR-2 on subcutaneous transplantation tumor model of human hepatoma cell Hep3B in immune deficiency mice was evaluated. The tumor volume of each treatment group at different time points is shown in Table 11 and FIG. 6. 44 days later after inoculation of Hep3B tumor cells, the tumor volume and tumor weight of the physiological saline control group reached 1984 $mm^3$ and 1555 mg, respectively.

The anti-tumor effect of 5-FU positive control group (15 mg/kg) was not significant with T/C value and p value of 106% and 0.996, respectively. The low dose (30 mg/kg) and high dose (45 mg/kg) group of LPR-2 had an anti-tumor effect slightly better than that of the 5-FU with tumor volume of 1074 and 827 $mm^3$, respectively, at the end of experiment, and T/C value of 54% and 42% and p value of 0.177 and 0.089, compared with the physiological saline group. The analysis result of tumor weight was consistent with the tumor volume.

Effect of changes in body weight of tumor-bearing mice in each group is shown in Table 10 and FIG. 5. The animals in each group had a declined body weight in the late stage of experiment which may be related to the tumor growth.

In summary, in this study, the test drug LPR-2 with dosages of 30 and 45 mg/kg showed a common anti-tumor effect on xenograft tumor model of human hepatoma cell Hep3B, and the animals administrated showed a good tolerance and no death of animals occurred.

Example 8 the Inhibitory Activity of Monomethoxy Polyethylene Glycol (with a Number Average Molecular Weight of 20,000)-Glutamic Acid Dipeptide-Rapamycin Conjugate (LPR-2) and Reference Substance Against H460 Human Non-Small Cell Lung Cancer Cells (1) Experimental Method and Procedure (a) Cell Culture H460 cells were cultured with a monolayer in vitro in RPMI1640 medium supplied with heat-inactivated fetal bovine serum with a volume ratio of 10%, and an incubator at 37° C. with the air containing $CO_2$ with a proportion of 5%. The tumor cells were passaged with digestion by trypsin-EDTA twice a week. The cells in the exponential growth phase were collected, counted, and used for inoculation.

(b) Inoculation of Tumor Cells, Grouping and Administration $5.0 \times 10^6$ of H460 tumor cells were suspended in 0.1 ml of PBS, inoculated to each nude mouse at the right shoulder, and there were totally 34 mice inoculated. 8 days later the mean tumor volume was desired to reach about 143 $mm^3$, the mice with a smaller or larger tumor were removed and the remaining 24 mice were divided into groups randomly according to tumor volume and administrated.

(c) Experimental Scheme

TABLE 13

The grouping and dosage regimen of experimental animals

| Group | N | Compound used for treatment | Dosage (mg/kg) | Dosing volume (μl/g) | Route of administration | Dosage regimen |
|---|---|---|---|---|---|---|
| 1 | 6 | Physiological saline | — | 10 | i.v. | QW × 3W |
| 2 | 6 | Paclitaxel | 15 | 10 | i.v. | BIW × 3W |
| 3 | 6 | LPR-2 | 30 | 10 | i.v. | BIW × 3W |
| 4 | 6 | LPR-2 | 45 | 15 | i.v. | QW × 3W |

(2) Experimental Results (a) Body Weight

LPR-2 and Paclitaxel had an effect on body weight of mice bearing xenograft tumor model of H460.

(c) Evaluation of Anti-Tumor Effect

The evaluation indexes of anti-tumor effect of LPR-2 and paclitaxel on xenograft tumor model of H460 are shown in Table 16.

TABLE 16

Evaluation of anti-tumor effect of each treatment group

| Group | $N^a$ | Tumor volume $(mm^3)^b$ | | $RTV^b$ | Tumor weight $(mg)^b$ | TGD (to 1,000 | T/C (%) | | P value | |
|---|---|---|---|---|---|---|---|---|---|---|
| | | $8^{th}$ day | $29^{th}$ day | ($29^{th}$ day) | ($29^{th}$ day) | $mm^3$) | RTV | $TW^c$ | RTV | $TW^c$ |
| physiological saline | 6 | 145 ± 21 | 2,157 ± 387 | 15.28 ± 2.40 | 1602 ± 354 | 0 | 100 | 100 | 1.000 | 1.000 |
| Paclitaxel (15 mg/kg) | 6 | 143 ± 15 | 1,281 ± 184 | 9.03 ± 0.93 | 1053 ± 146 | 7 | 59 | 66 | 0.212 | 0.061 |
| LPR-2 (30 mg/kg) BIW × 3W | 6 | 143 ± 16 | 505 ± 87 | 3.43 ± 0.32 | 364 ± 54 | >9 | 22 | 23 | 0.019 | 0.000 |
| LPR-2 (45 mg/kg) QW × 3W | 6 | 143 ± 18 | 549 ± 76 | 3.86 ± 0.42 | 406 ± 60 | >9 | 25 | 25 | 0.022 | 0.000 |

Note:
[a] the number of surviving animals in each group after completion of the treatment;
[b] Mean ± SEM;
[c] TW (Tumor Weight).

Figure 7:
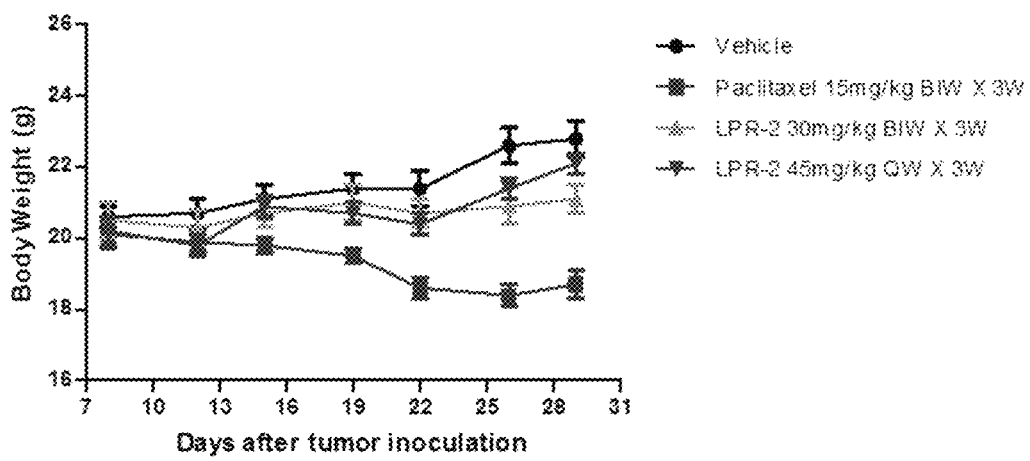
FIG. 7 shows the results of change in body weight of mice bearing human non-small cell lung cancer cell H460 caused by LPR-2 and reference substance.

Changes in body weight of tumor-bearing mice in each treatment group are shown in Table 14 and FIG. 7.

TABLE 14

The weight of each treatment group at different time points

| | Body weight of animal (g)$^a$ | | | |
|---|---|---|---|---|
| Days after inoculation | Physiological saline | Paclitaxel 15 mg/kg | LPR-2 30 mg/kg BIW × 3W | LPR-2 45 mg/kg QW × 3W |
| 8 | 20.6 ± 0.3 | 20.1 ± 0.4 | 20.5 ± 0.5 | 20.2 ± 0.4 |
| 12 | 20.7 ± 0.4 | 19.9 ± 0.3 | 20.3 ± 0.5 | 19.8 ± 0.3 |
| 15 | 21.1 ± 0.4 | 19.8 ± 0.2 | 20.7 ± 0.4 | 20.9 ± 0.3 |
| 19 | 21.4 ± 0.4 | 19.5 ± 0.2 | 21.0 ± 0.5 | 20.7 ± 0.3 |
| 22 | 21.4 ± 0.5 | 18.6 ± 0.3 | 20.7 ± 0.4 | 20.4 ± 0.3 |
| $26^b$ | 22.6 ± 0.5 | 18.4 ± 0.3 | 20.9 ± 0.5 | 21.4 ± 0.3 |
| 29 | 22.8 ± 0.5 | 18.7 ± 0.4 | 21.1 ± 0.4 | 22.1 ± 0.3 |

Note:
[a] mean value ± standard error;
[b] last administration.

(b) Tumor Growth

TABLE 15

The tumor volume of each treatment group at different time points

| | Tumor volume $(mm^3)^a$ | | | |
|---|---|---|---|---|
| Days after inoculation | Physiological saline | Paclitaxel 15 mg/kg | LPR-2 30 mg/kg BIW × 3W | LPR-2 45 mg/kg QW × 3W |
| 8 | 145 ± 21 | 143 ± 15 | 143 ± 16 | 143 ± 18 |
| 12 | 391 ± 66 | 295 ± 42 | 213 ± 40 | 194 ± 33 |
| 15 | 595 ± 112 | 400 ± 70 | 208 ± 44 | 260 ± 46 |
| 19 | 905 ± 149 | 519 ± 97 | 259 ± 50 | 282 ± 46 |
| 22 | 1,176 ± 180 | 680 ± 110 | 343 ± 67 | 346 ± 53 |
| $26^b$ | 1,643 ± 286 | 944 ± 117 | 459 ± 70 | 468 ± 57 |
| 29 | 2,157 ± 387 | 1,281 ± 184 | 505 ± 87 | 549 ± 76 |

Note:
[a] mean value ± standard error;
[b] last administration.

(3) Summary and Discussion of Experimental Results

Figure 8:
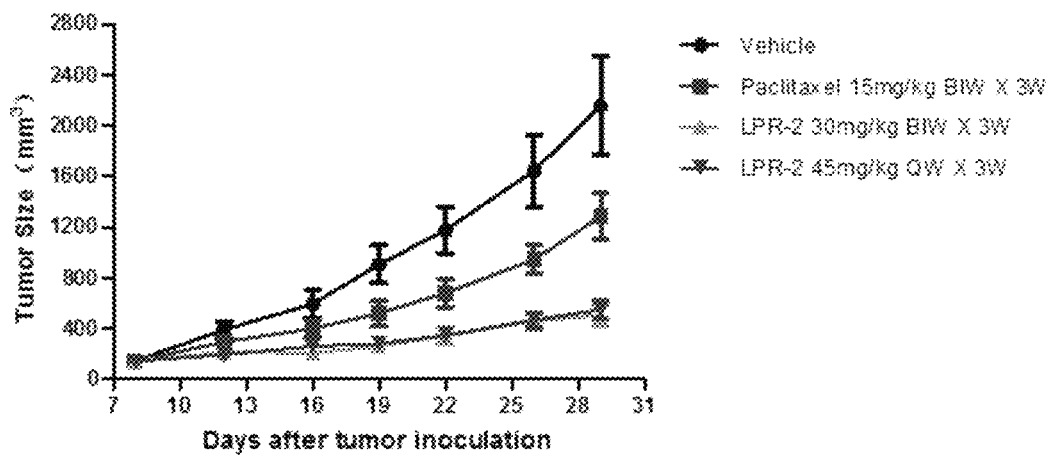
FIG. 8 shows the results of antitumor activity of LPR-2 and reference substance against subcutaneous transplantation tumor model of human non-small cell lung cancer cell H460.

In the experiment, the pesticide effect in vivo of LPR-2 on subcutaneous transplantation tumor model of H460 human non-small cell lung cancer in nude mice was evaluated. The tumor volume of each treatment group at different time points is shown in Table 15 and FIG. 8. 29 days later after inoculation of H460 tumor cells, the tumor volume and tumor weight of the physiological saline control group reached 2157 mm$^3$ and 1602 mg, respectively.

The paclitaxe positive control group of showed a certain anti-tumor effect with a T/C value of 59% and p value of 0.212.

The two groups of LPR-2 with different dosages (30 and 45 mg/kg) showed a significant anti-tumor effect with tumor volume of 505 and 549 mm$^3$, respectively, at the end of experiment, and T/C value of 22% and 25% and p value of 0.019 and 0.022, compared with the physiological saline group. The analysis result of tumor weight was consistent with the tumor volume.

Effect of changes in body weight of tumor-bearing mice in each group is shown in Table 14 and FIG. 7. In paclitaxel administration group, animals appeared to wheeze and hold still after being administrated and returned to normal after half an hour, and had a declined body weight in the late stage of administration. No abnormality in each group administrated with LPR-2 before or after administration was observed and body weight remained stable during the administration period. No animals died in this experiment.

In summary, in this study, the test drug LPR-2 with dosages of 30 and 45 mg/kg showed a significant anti-tumor effect on xenograft tumor model of H460 human non-small cell lung cancer, and the animals administrated showed a good tolerance and no death of animals occurred.

Example 9 the Inhibitory Activity of Monomethoxy Polyethylene Glycol (with a Number Average Molecular Weight of 20,000)-Glutamic Acid Dipeptide-Rapamycin Conjugate (LPR-2) and Reference Substance Against Calu-6 Human Lung Cells (1) Experimental Method and Procedure (a) Cell Culture Calu-6 cells were cultured with a monolayer in vitro in MEM medium supplied with heat-inactivated fetal bovine serum with a volume ratio of 10%, and an incubator at 37° C. with the air containing $CO_2$ with a proportion of 5%. The tumor cells were passaged with digestion by trypsin-EDTA twice a week. The cells in the exponential growth phase were collected, counted, and used for inoculation.

(b) Inoculation of Tumor Cells, Grouping and Administration $5.0 \times 10^6$ of Calu-6 tumor cells were suspended in 0.1 ml of PBS, inoculated to each nude mouse at the right shoulder, and there were totally 34 mice inoculated. 14 days later the mean tumor volume was desired to reach about 138 mm³, the mice with a smaller or larger tumor were removed and the remaining 24 mice were divided into groups randomly according to tumor volume and administrated.

(c) Experimental Scheme

TABLE 17

The grouping and dosage regimen of experimental animals

| Group | N | Compound used for treatment | Dosage (mg/kg) | Dosing volume (μl/g) | Route of administration | Dosage regimen |
|---|---|---|---|---|---|---|
| 1 | 6 | Physiological saline | — | 10 | i.v. | QW × 4W |
| 2 | 6 | Paclitaxel | 15 | 10 | i.v. | BIW × 4W |
| 3 | 6 | LPR-2 | 30 | 10 | i.v. | BIW × 4W |
| 4 | 6 | LPR-2 | 45 | 15 | i.v. | QW × 4W |

(2) Experimental Results (a) Body Weight

LPR-2 and paclitaxel had an effect on body weight of mice bearing xenograft tumor model of Calu-6.

Figure 9:
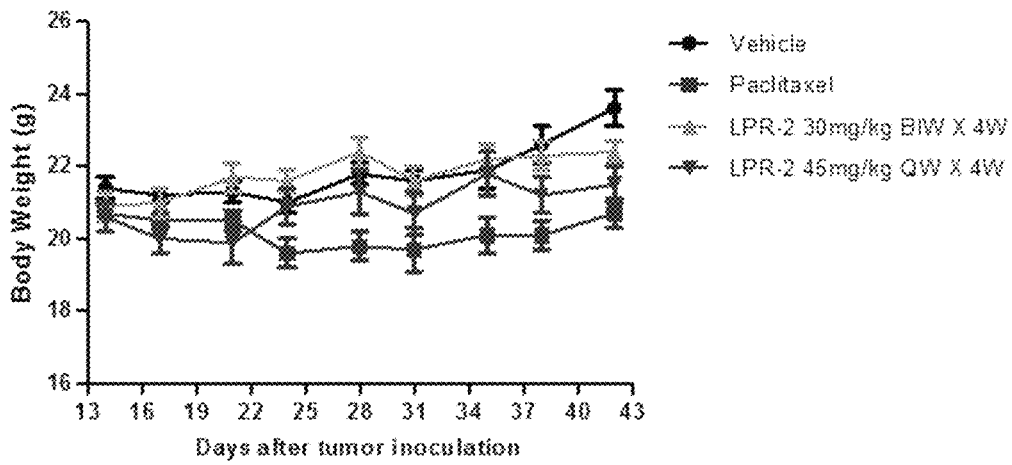
FIG. 9 shows the results of change in body weight of mice bearing human lung cell Calu-6 caused by LPR-2 and reference substance.

Changes in body weight of tumor-bearing mice in each treatment group are shown in Table 18 and FIG. 9.

TABLE 18

The weight of each treatment group at different time points

| | Body weight of animal (g)[a] | | | |
|---|---|---|---|---|
| Days after inoculation | Physiological saline | Paclitaxel 15 mg/kg | LPR-2 30 mg/kg BIW × 4W | LPR-2 45 mg/kg QW × 4W |
| 14 | 21.4 ± 0.3 | 20.7 ± 0.2 | 20.9 ± 0.4 | 20.6 ± 0.4 |
| 17 | 21.2 ± 0.2 | 20.5 ± 0.2 | 21.0 ± 0.4 | 20.0 ± 0.4 |
| 21 | 21.3 ± 0.3 | 20.5 ± 0.3 | 21.7 ± 0.4 | 19.9 ± 0.6 |
| 24 | 21.0 ± 0.3 | 19.6 ± 0.4 | 21.6 ± 0.3 | 20.9 ± 0.5 |
| 28 | 21.8 ± 0.3 | 19.8 ± 0.4 | 22.4 ± 0.4 | 21.3 ± 0.6 |
| 31 | 21.6 ± 0.3 | 19.7 ± 0.6 | 21.6 ± 0.4 | 20.7 ± 0.6 |
| 35 | 21.9 ± 0.5 | 20.1 ± 0.5 | 22.2 ± 0.4 | 21.8 ± 0.6 |
| 38[b] | 22.6 ± 0.5 | 20.1 ± 0.4 | 22.3 ± 0.4 | 21.2 ± 0.5 |
| 42 | 23.6 ± 0.5 | 20.7 ± 0.4 | 22.4 ± 0.3 | 21.5 ± 0.5 |

Note:
[a]mean value ± standard error;
[b]last administration.

(b) Tumor Growth

Figure 10:
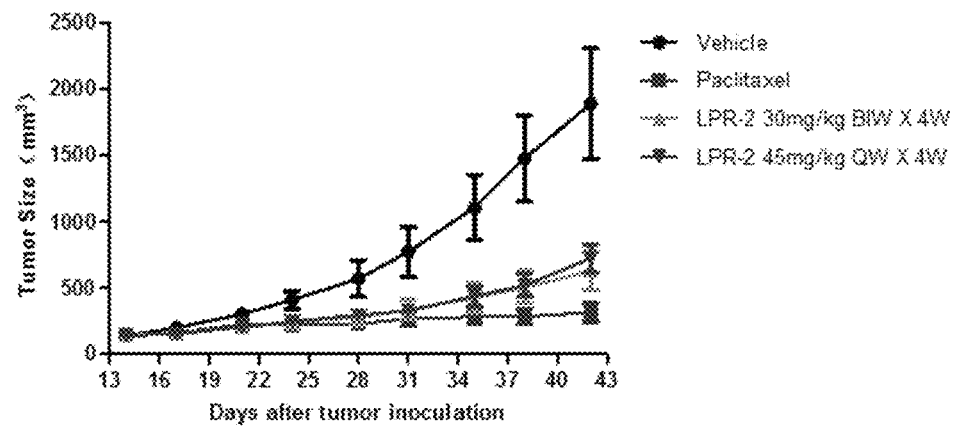
FIG. 10 shows the results of antitumor activity of LPR-2 and reference substance against subcutaneous transplantation tumor model of human lung cell Calu-6.

Changes in tumor volume of each treatment group are shown in Table 19 and FIG. 10.

TABLE 19

The tumor volume of each treatment group at different time points

| | Tumor volume (mm³)[a] | | | |
|---|---|---|---|---|
| Days after inoculation | Physiological saline | Paclitaxel 15 mg/kg | LPR-2 30 mg/kg BIW × 4W | LPR-2 45 mg/kg QW × 4W |
| 14 | 138 ± 20 | 138 ± 14 | 139 ± 18 | 137 ± 22 |
| 17 | 196 ± 23 | 159 ± 18 | 160 ± 25 | 152 ± 25 |
| 21 | 301 ± 28 | 222 ± 23 | 201 ± 40 | 204 ± 38 |
| 24 | 407 ± 68 | 219 ± 26 | 241 ± 50 | 245 ± 40 |
| 28 | 568 ± 137 | 229 ± 37 | 274 ± 57 | 293 ± 44 |
| 31 | 769 ± 188 | 264 ± 53 | 335 ± 76 | 323 ± 45 |
| 35 | 1,108 ± 246 | 281 ± 59 | 422 ± 108 | 436 ± 74 |
| 38[b] | 1,474 ± 325 | 282 ± 60 | 504 ± 119 | 518 ± 87 |
| 42 | 1,889 ± 416 | 314 ± 72 | 627 ± 145 | 720 ± 106 |

Note:
[a]mean value ± standard error;
[b]last administration.

(c) Evaluation of Anti-Tumor Effect

The evaluation indexes of anti-tumor effect of LPR-2 and paclitaxel on xenograft tumor model of calu-6 are shown in Table 24.

TABLE 20

Evaluation of anti-tumor effect of each treatment group

| Group | N[a] | Tumor volume (mm³)[b] 14th day | Tumor volume (mm³)[b] 42nd day | RTV[b] (42nd day) | Tumor weight (mg)[b] (42nd day) | TGD (to 1,000 mm³) | T/C (%) RTV | T/C (%) TW[c] | P value RTV | P value TW[c] |
|---|---|---|---|---|---|---|---|---|---|---|
| physiological saline | 6 | 138 ± 20 | 1,889 ± 416 | 14.29 ± 2.45 | 1616 ± 369 | 0 | 100 | 100 | 1.000 | 1.000 |
| Paclitaxel (15 mg/kg) | 6 | 138 ± 14 | 314 ± 72 | 2.31 ± 0.53 | 202 ± 52 | >8 | 16 | 13 | 0.019 | 0.054 |
| LPR-2 (30 mg/kg) BIW × 4W | 6 | 139 ± 18 | 627 ± 145 | 4.39 ± 0.59 | 449 ± 89 | >8 | 31 | 28 | 0.042 | 0.107 |
| LPR-2 (45 mg/kg) QW × 4W | 6 | 137 ± 22 | 720 ± 106 | 5.41 ± 0.51 | 602 ± 83 | >8 | 38 | 37 | 0.065 | 0.170 |

Note:
[a] the number of surviving animals in each group after completion of the treatment;
[b] Mean ± SEM;
[c] TW (Tumor Weight).

(3) Summary and Discussion of Experimental Results

In the experiment, the pesticide effect in vivo of LPR-2 on subcutaneous transplantation tumor model of calu-6 human lung cancer cell in nude mice was evaluated. The tumor volume of each treatment group at different time points is shown in Table 19 and FIG. 10. 42 days later after inoculation of calu-6 tumor cells, the tumor volume and tumor weight of the physiological saline control group reached 1889 mm³ and 1616 mg, respectively.

The paclitaxel positive control group showed a significant anti-tumor effect with a T/C value of 16% and p value of 0.019.

The two groups of LPR-2 with different dosages (30 and 45 mg/kg) showed a significant anti-tumor effect with tumor volume of 449 and 602 mm³, respectively, at the end of experiment, and T/C value of 31% and 38% and p value of 0.042 and 0.065, compared with the physiological saline group.

The analysis result of tumor weight was basically consistent with relative tumor proliferation rate, however, compared with the control group, no significant difference was obtained from the analysis for statistical results of paclitaxel and LPR-2 (30 mg/kg, BIW×4W) due to a large difference between tumor weight data in each experimental group.

Effect of changes in body weight of tumor-bearing mice in each group is shown in Table 18 and FIG. 9. In paclitaxel administration group, animals appeared to wheeze and hold still after being administrated and returned to normal after half an hour. No abnormality in each group administrated with LPR-2 before or after administration was observed. The body weight of each experimental group remained stable during the administration period and no animals died in this experiment.

In summary, in this study, the test drug LPR-2 with dosages of 30 and 45 mg/kg showed a significant anti-tumor effect on xenograft tumor model of calu-6 human lung cancer cell, and the animals administrated showed a good tolerance and no death of animals occurred.

Example 10 the Inhibitory Activity of Monomethoxy Polyethylene Glycol (with a Number Average Molecular Weight of 20,000)-Glutamic Acid Dipeptide-Rapamycin Conjugate (LPR-2) and Reference Substance Against A549 Human Non-Small Cell Lung Cancer Cells (1) Experimental Method and Procedure (a) Cell Culture A549 cells were cultured with a monolayer in vitro in RPMI1640 medium supplied with heat-inactivated fetal bovine serum with a volume ratio of 10%, and an incubator at 37° C. with the air containing $CO_2$ with a proportion of 5%. The tumor cells were passaged with digestion by trypsin-EDTA twice a week. The cells in the exponential growth phase were collected, counted, and used for inoculation.

(b) Inoculation of Tumor Cells, Grouping and Administration $1.0 \times 10^7$ of A549 tumor cells were suspended in 0.1 ml of PBS, inoculated to each nude mouse at the right shoulder, and there were totally 36 mice inoculated. 24 days later the mean tumor volume was desired to reach about 138 mm³, the mice with a smaller or larger tumor were removed and the remaining 24 mice were divided into groups randomly according to tumor volume and administrated.

(c) Experimental Scheme

TABLE 21

The grouping and dosage regimen of experimental animals

| Group | N | Compound used for treatment | Dosage (mg/kg) | Dosing volume (μl/g) | Route of administration | Dosage regimen |
|---|---|---|---|---|---|---|
| 1 | 6 | Physiological saline | — | 10 | i.v. | QW × 4W |
| 2 | 6 | Paclitaxel | 15 | 10 | i.v. | BIW × 4W |
| 3 | 6 | LPR-2 | 30 | 10 | i.v. | BIW × 4W |
| 4 | 6 | LPR-2 | 45 | 15 | i.v. | QW × 4W |

(2) Experimental Results (a) Body Weight

LPR-2 and paclitaxel had an effect on body weight of mice bearing xenograft tumor model of A549.

Figure 11:
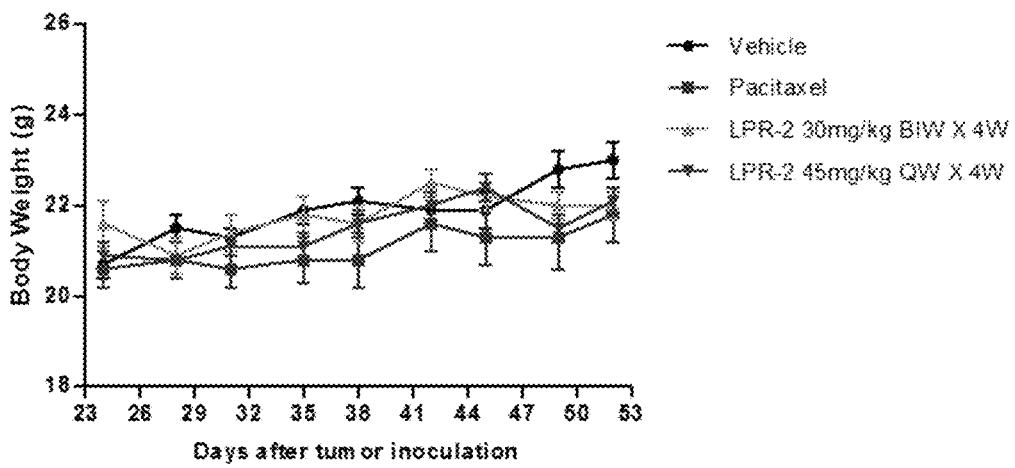
FIG. 11 shows the results of change in body weight of mice bearing human non-small cell lung cancer cell A549 caused by LPR-2 and reference substance.

Changes in body weight of tumor-bearing mice in each treatment group are shown in Table 22 and FIG. 11.

TABLE 22

The weight of each treatment group at different time points

| Days after inoculation | Body weight of animal (g)[a] | | | |
|---|---|---|---|---|
| | Physiological saline | Paclitaxel 15 mg/kg | LPR-2 30 mg/kg BIW × 4W | LPR-2 45 mg/kg QW × 4W |
| 24 | 20.7 ± 0.3 | 20.6 ± 0.4 | 21.6 ± 0.5 | 20.9 ± 0.3 |
| 28 | 21.5 ± 0.3 | 20.8 ± 0.4 | 20.9 ± 0.4 | 20.8 ± 0.1 |
| 31 | 21.3 ± 0.2 | 20.6 ± 0.4 | 21.4 ± 0.4 | 21.1 ± 0.2 |
| 35 | 21.9 ± 0.3 | 20.8 ± 0.5 | 21.8 ± 0.4 | 21.1 ± 0.3 |
| 38 | 22.1 ± 0.3 | 20.8 ± 0.6 | 21.6 ± 0.4 | 21.6 ± 0.3 |
| 42 | 21.9 ± 0.3 | 21.6 ± 0.6 | 22.5 ± 0.3 | 22.0 ± 0.3 |
| 45 | 21.9 ± 0.4 | 21.3 ± 0.6 | 22.2 ± 0.3 | 22.4 ± 0.3 |

TABLE 22-continued

The weight of each treatment group at different time points

| Days after inoculation | Body weight of animal (g)[a] | | | |
|---|---|---|---|---|
| | Physiological saline | Paclitaxel 15 mg/kg | LPR-2 30 mg/kg BIW × 4W | LPR-2 45 mg/kg QW × 4W |
| 49[b] | 22.8 ± 0.4 | 21.3 ± 0.7 | 22.0 ± 0.3 | 21.5 ± 0.3 |
| 52 | 23.0 ± 0.4 | 21.8 ± 0.6 | 22.0 ± 0.3 | 22.1 ± 0.3 |

Note:
[a]mean value ± standard error;
[b]last administration.

(b) Tumor Growth

Figure 12:
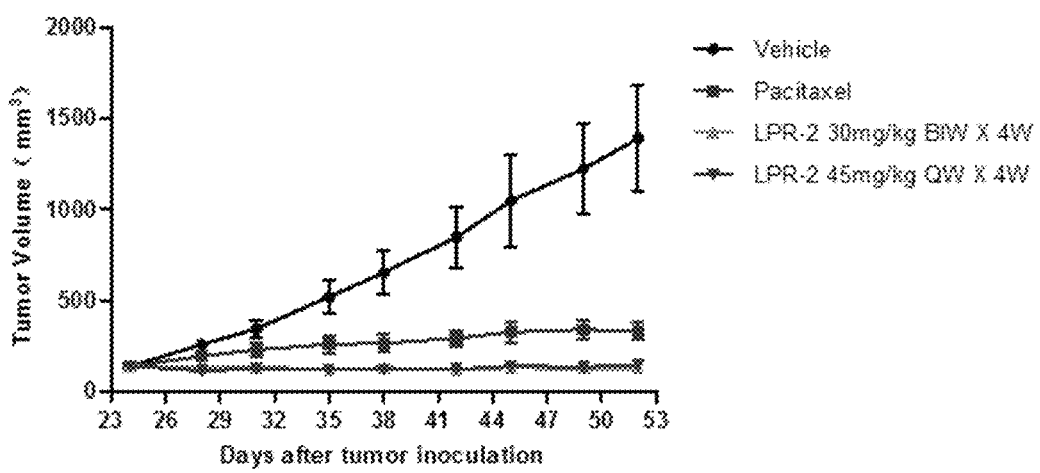
FIG. 12 shows the results of antitumor activity of LPR-2 and reference substance against subcutaneous transplantation tumor model of human non-small cell lung cancer cell A549.

Changes in tumor volume of each treatment group are shown in Table 23 and FIG. 12.

TABLE 23

The tumor volume of each treatment group at different time points

| Days after inoculation | Tumor volume (mm$^3$)[a] | | | |
|---|---|---|---|---|
| | Physiological saline | Paclitaxel 15 mg/kg | LPR-2 30 mg/kg BIW × 4W | LPR-2 45 mg/kg QW × 4W |
| 24 | 138 ± 13 | 138 ± 13 | 140 ± 11 | 139 ± 11 |
| 28 | 259 ± 28 | 196 ± 24 | 131 ± 8 | 115 ± 8 |
| 31 | 345 ± 50 | 230 ± 35 | 134 ± 11 | 126 ± 10 |
| 35 | 521 ± 87 | 260 ± 49 | 124 ± 15 | 122 ± 13 |
| 38 | 654 ± 120 | 265 ± 48 | 131 ± 13 | 120 ± 13 |
| 42 | 849 ± 167 | 294 ± 41 | 122 ± 8 | 124 ± 9 |
| 45 | 1,047 ± 254 | 327 ± 54 | 131 ± 9 | 140 ± 11 |
| 49[b] | 1,224 ± 251 | 342 ± 54 | 128 ± 9 | 138 ± 14 |
| 52 | 1,391 ± 288 | 331 ± 49 | 127 ± 6 | 145 ± 14 |

Note:
[a]mean value ± standard error;
[b]last administration.

(c) Evaluation of Anti-Tumor Effect

The evaluation indexes of anti-tumor effect of LPR-2 and paclitaxel on xenograft tumor model of A549 are shown in Table 24.

TABLE 24

Evaluation of anti-tumor effect of each treatment group

| Group | N[a] | Tumor volume (mm$^3$)[b] | | RTV[b] | Tumor weight (mg)[b] | TGD (to 1,000 | T/C (%) | | P value | |
| | | 24$^{th}$ day | 52$^{nd}$ day | (52$^{nd}$ day) | (52$^{nd}$ day) | mm$^3$) | RTV | TW[c] | RTV | TW[c] |
|---|---|---|---|---|---|---|---|---|---|---|
| Physiological saline | 6 | 138 ± 13 | 1,391 ± 288 | 9.81 ± 1.50 | 1302 ± 326 | 0 | 100 | 100 | 1.000 | 1.000 |
| Paclitaxel (15 mg/kg) | 6 | 138 ± 13 | 331 ± 49 | 2.35 ± 0.16 | 253 ± 52 | >7 | 24 | 19 | 0.019 | 0.101 |
| LPR-2 (30 mg/kg) BIW × 4W | 6 | 140 ± 11 | 127 ± 6 | 0.94 ± 0.11 | 102 ± 15 | >7 | 10 | 8 | 0.009 | 0.063 |
| LPR-2 (45 mg/kg) QW × 4W | 6 | 139 ± 11 | 145 ± 14 | 1.05 ± 0.11 | 129 ± 20 | >7 | 11 | 10 | 0.010 | 0.069 |

Note:
[a]the number of surviving animals in each group after completion of the treatment;
[b]Mean ± SEM;
[c]TW (Tumor Weight).

(3) Summary and Discussion of Experimental Results

In the experiment, the pesticide effect in vivo of LPR-2 on subcutaneous transplantation tumor model of A549 human non-small cell lung cancer in nude mice was evaluated. The tumor volumes of each treatment group at different time points are shown in Table 23 and FIG. 12. 52 days later after inoculation of A549 tumor cells, the tumor volume and tumor weight of the physiological saline control group reached 1351 mm$^3$ and 1302 mg, respectively.

The paclitaxel positive control group showed a significant anti-tumor effect with a T/C value of 24% and p value of 0.019.

The two groups of LPR-2 with different dosages (30 and 45 mg/kg) showed a significant anti-tumor effect with tumor volume of 127 and 145 mm$^3$, respectively, at the end of experiment, and T/C value of 10% and 11% and p value of 0.009 and 0.010, compared with the physiological saline group.

The analysis result of tumor weight was basically consistent with relative tumor proliferation rate, however, compared with the control group, no significant difference was obtained from the analysis for statistical results of each administration group due to a large difference between tumor weight data in each experimental group.

Effect of changes in body weight of tumor-bearing mice in each group is shown in Table 22 and FIG. 11. In paclitaxel administration group, animals appeared to wheeze and hold still after being administrated and returned to normal after half an hour. No abnormality in each group administrated with LPR-2 before or after administration was observed. The body weight of each experimental group remained stable during the administration period and no animals died in this experiment.

In summary, in this study, the test drug LPR-2 with dosages of 30 and 45 mg/kg showed a significant anti-tumor effect on xenograft tumor model of A549 human non-small cell lung cancer, and the animals administrated showed a good tolerance and no death of animals occurred.

The invention claimed is:

1. A compound or a pharmaceutically acceptable salt thereof, wherein the compound comprises rapamycin conjugated to polyethylene glycol (PEG) and has the following formula:

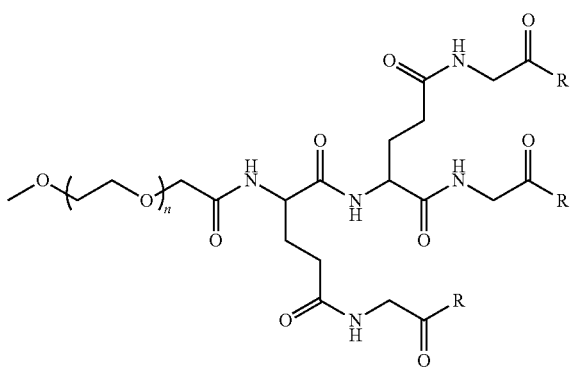

R =

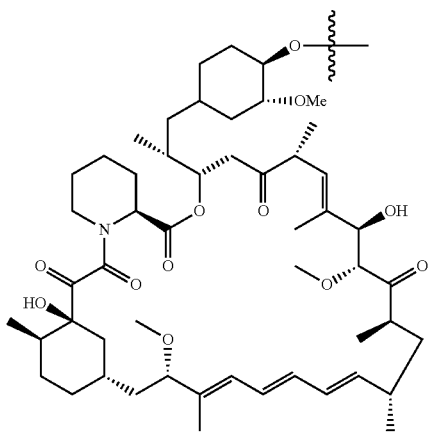

and wherein the PEG has a number average molecular weight of 20,000 Daltons.

2. A method of treating and/or inhibiting graft rejection in a subject in need thereof, the method comprising administering to the subject the compound of claim 1 or a pharmaceutically acceptable salt thereof.

3. A method of treating rheumatoid arthritis in a subject in need thereof, the method comprising administering to the subject the compound of claim 1 or a pharmaceutically acceptable salt thereof.

4. A method of treating solid tumor in a subject in need thereof, the method comprising administering to the subject the compound of claim 1 or a pharmaceutically acceptable salt thereof, wherein the solid tumor is selected from the group consisting of astrocytoma, liver cancer, prostate cancer, breast cancer, lung cancer and ovarian cancer.

* * * * *